US012618858B2

(12) United States Patent
Koussa

(10) Patent No.: US 12,618,858 B2
(45) Date of Patent: May 5, 2026

(54) KINETIC MODULATION FOR MAGNETIC ANALYTE DETECTION

(71) Applicant: Vital Biosciences Inc., Mississauga (CA)

(72) Inventor: Mounir A. Koussa, Mississauga (CA)

(73) Assignee: Vital Biosciences Inc., Mississauga (CA)

( * ) Notice: Subject to any disclaimer, the term of this patent is extended or adjusted under 35 U.S.C. 154(b) by 343 days.

(21) Appl. No.: 18/019,677

(22) PCT Filed: Aug. 7, 2021

(86) PCT No.: PCT/IB2021/057295
§ 371 (c)(1),
(2) Date: Feb. 3, 2023

(87) PCT Pub. No.: WO2022/029732
PCT Pub. Date: Feb. 10, 2022

(65) Prior Publication Data
US 2023/0324416 A1 Oct. 12, 2023

Related U.S. Application Data

(60) Provisional application No. 63/063,029, filed on Aug. 7, 2020.

(51) Int. Cl.
*G01N 33/76* (2006.01)
*G01N 33/543* (2006.01)
(52) U.S. Cl.
CPC ....... *G01N 33/76* (2013.01); *G01N 33/54333* (2013.01); *G01N 2470/04* (2021.08)
(58) Field of Classification Search
CPC ............. G01N 33/76; G01N 33/54333; G01N 2470/04; G01N 33/54388; G01N 33/54393; G01N 33/54326

USPC .......................................................... 436/87
See application file for complete search history.

(56) References Cited

U.S. PATENT DOCUMENTS

| | | | |
|---|---|---|---|
| 4,141,687 A | 2/1979 | Forrest et al. |
| 4,630,691 A | 12/1986 | Hooper |
| 4,972,907 A | 11/1990 | Sellars et al. |
| 5,256,543 A | 10/1993 | Pouletty et al. |
| 5,683,875 A | 11/1997 | Lichtenwalter |
| 5,776,487 A | 7/1998 | Maxfield Wilson et al. |
| 5,807,758 A | 9/1998 | Lee et al. |
| 5,945,345 A | 8/1999 | Blatt et al. |

(Continued)

FOREIGN PATENT DOCUMENTS

| | | |
|---|---|---|
| CN | 1700009 A | 11/2005 |
| CN | 101438163 A | 5/2009 |

(Continued)

OTHER PUBLICATIONS

International Search Report & Written Opinion, PCT Application No. PCT/IB/2021/057295, dated Nov. 8, 2021, 13 pages.

(Continued)

*Primary Examiner* — Christine T Mui
(74) *Attorney, Agent, or Firm* — Morgan, Lewis & Bockius LLP

(57) ABSTRACT

Methods and kits for detection of presence, absence, or amount of an analyte in a biological sample are provided. In the methods and kits, kinetics of the detection is modulated my adjusting concentrations of a reporter binding moiety and a reporter.

12 Claims, 7 Drawing Sheets

Specification includes a Sequence Listing.

(56)        References Cited

U.S. PATENT DOCUMENTS

| | | | |
|---|---|---|---|
| 5,948,624 A | 9/1999 | Rothschild et al. |
| 5,993,740 A | 11/1999 | Niiyama et al. |
| 6,103,537 A | 8/2000 | Ullman et al. |
| 6,143,493 A | 11/2000 | Stüber et al. |
| 6,265,229 B1 | 7/2001 | Fodstad et al. |
| 6,274,323 B1 | 8/2001 | Bruchez et al. |
| 6,291,249 B1 | 9/2001 | Mahant et al. |
| 6,361,958 B1 | 3/2002 | Shieh et al. |
| 6,417,011 B1 | 7/2002 | Miltenyi |
| 6,444,261 B1 | 9/2002 | Plaksine et al. |
| 6,468,657 B1 | 10/2002 | Hou et al. |
| 6,479,302 B1 | 11/2002 | Dremel |
| 6,551,841 B1 | 4/2003 | Wilding et al. |
| 6,569,647 B1 | 5/2003 | Zhang et al. |
| 6,607,922 B2 | 8/2003 | LaBorde |
| 6,649,419 B1 | 11/2003 | Anderson |
| 6,746,661 B2 | 6/2004 | Kaplan |
| 6,930,292 B1 | 8/2005 | Winther et al. |
| 6,960,467 B2 | 11/2005 | Shieh et al. |
| 7,005,292 B2 | 2/2006 | Wilding et al. |
| 7,018,830 B2 | 3/2006 | Wilding et al. |
| 7,074,586 B1 | 7/2006 | Cheronis et al. |
| 7,113,069 B1 | 9/2006 | Sunshine et al. |
| 7,179,660 B1 | 2/2007 | Kirakossian et al. |
| 7,271,265 B2 | 9/2007 | Haugland et al. |
| 7,413,909 B2 | 8/2008 | Hutchens et al. |
| 7,416,889 B2 | 8/2008 | Ciomber et al. |
| 7,510,865 B2 | 3/2009 | Yoo et al. |
| 7,527,980 B2 | 5/2009 | Haik |
| 7,572,640 B2 | 8/2009 | Goix et al. |
| 7,635,585 B2 | 12/2009 | Yoo |
| 7,718,421 B2 | 5/2010 | Chen et al. |
| 7,732,153 B2 | 6/2010 | Akhavan-Tafti |
| 7,799,534 B2 | 9/2010 | Akhavan-Tafti |
| 7,838,250 B1 | 11/2010 | Goix et al. |
| 7,842,515 B2 | 11/2010 | Zou et al. |
| 7,855,054 B2 | 12/2010 | Schneider et al. |
| 7,863,022 B2 | 1/2011 | Prins et al. |
| 7,914,734 B2 | 3/2011 | Livingston |
| 7,923,213 B2 | 4/2011 | Akhavan-Tafti |
| 7,923,214 B2 | 4/2011 | Akhavan-Tafti |
| 8,076,092 B2 | 12/2011 | Akhavan-Tafti |
| 8,088,586 B2 | 1/2012 | Barnardo et al. |
| 8,101,138 B2 | 1/2012 | Lee et al. |
| 8,124,362 B2 | 2/2012 | Tafti |
| 8,188,243 B2 | 5/2012 | Bard et al. |
| 8,190,372 B2 | 5/2012 | Kahlman et al. |
| 8,263,386 B2 | 9/2012 | Yoo |
| 8,264,684 B2 | 9/2012 | Livingston |
| 8,278,057 B2 | 10/2012 | Singh et al. |
| 8,283,912 B2 | 10/2012 | Nieuwenhuis et al. |
| 8,287,809 B2 | 10/2012 | Gould et al. |
| 8,287,810 B2 | 10/2012 | Alocilja et al. |
| 8,318,445 B2 | 11/2012 | Bernard et al. |
| 8,343,728 B2 | 1/2013 | Goix et al. |
| 8,357,671 B2 | 1/2013 | Paulson et al. |
| 8,409,877 B2 | 4/2013 | Liu et al. |
| 8,449,833 B2 | 5/2013 | Nieuwenhuis |
| 8,450,069 B2 | 5/2013 | Goix et al. |
| 8,462,339 B2 | 6/2013 | Livingston |
| 8,512,966 B2 | 8/2013 | Carter et al. |
| 8,520,211 B2 | 8/2013 | Schleipen et al. |
| 8,524,504 B2 | 9/2013 | Carter et al. |
| 8,535,895 B2 | 9/2013 | Goix et al. |
| 8,617,798 B2 | 12/2013 | Mason et al. |
| 8,618,508 B2 | 12/2013 | Wimberger-Friedl et al. |
| 8,628,729 B2 | 1/2014 | Carrilho et al. |
| 8,634,075 B2 | 1/2014 | Livingston |
| 8,664,008 B2 | 3/2014 | Liu et al. |
| 8,669,110 B2 | 3/2014 | Dehal et al. |
| 8,685,711 B2 | 4/2014 | Goix et al. |
| 8,758,686 B2 | 6/2014 | Carter et al. |
| 8,797,028 B2 | 8/2014 | Verschuren et al. |
| 8,828,740 B2 | 9/2014 | Kahlman et al. |
| 8,841,070 B2 | 9/2014 | Harnack et al. |
| 8,871,917 B2 | 10/2014 | Bard et al. |
| 8,873,038 B2 | 10/2014 | Kodali et al. |
| 8,917,392 B2 | 12/2014 | Livingston |
| 8,921,118 B2 | 12/2014 | Siegel et al. |
| 8,932,811 B2 | 1/2015 | Van De Stolpe et al. |
| 8,936,946 B2 | 1/2015 | Alocilja et al. |
| 8,951,749 B2 | 2/2015 | Rylatt et al. |
| 8,986,926 B2 | 3/2015 | Ferree et al. |
| 8,993,487 B2 | 3/2015 | Yoo |
| 9,023,651 B2 | 5/2015 | Evers et al. |
| 9,040,305 B2 | 5/2015 | Goix et al. |
| 9,046,514 B2 | 6/2015 | Sista et al. |
| 9,056,318 B2 | 6/2015 | Bergman et al. |
| 9,057,723 B2 | 6/2015 | Carter et al. |
| 9,063,131 B2 | 6/2015 | Goix et al. |
| 9,068,991 B2 | 6/2015 | Goix et al. |
| 9,075,041 B2 | 7/2015 | Kavusi et al. |
| 9,101,301 B2 | 8/2015 | Papadimitrakopoulos et al. |
| 9,103,843 B2 | 8/2015 | Nieuwenhuis et al. |
| 9,128,084 B2 | 9/2015 | Prins et al. |
| 9,134,201 B2 | 9/2015 | Van Lankvelt et al. |
| 9,157,891 B2 | 10/2015 | Ovsyanko et al. |
| 9,164,091 B2 | 10/2015 | Kim |
| 9,180,453 B2 | 11/2015 | Chiu et al. |
| 9,182,405 B2 | 11/2015 | Goix et al. |
| 9,207,210 B2 | 12/2015 | Ovsyanko |
| 9,239,284 B2 | 1/2016 | Livingston |
| 9,254,488 B2 | 2/2016 | Nieuwenhuis et al. |
| 9,267,167 B2 | 2/2016 | Lizzi et al. |
| 9,274,105 B2 | 3/2016 | Guo et al. |
| 9,304,130 B2 | 4/2016 | Boday et al. |
| 9,328,343 B2 | 5/2016 | Dressman et al. |
| 9,329,175 B2 | 5/2016 | Miller et al. |
| 9,333,276 B2 | 5/2016 | Guelcher et al. |
| 9,371,563 B2 | 6/2016 | Geiss et al. |
| 9,371,596 B2 | 6/2016 | Faure et al. |
| 9,387,484 B2 | 7/2016 | Wimberger-Friedl et al. |
| 9,404,919 B2 | 8/2016 | Schneider et al. |
| 9,410,948 B2 | 8/2016 | Dittmer |
| 9,442,117 B2 | 9/2016 | Bard et al. |
| 9,448,236 B2 | 9/2016 | Alocilja et al. |
| 9,488,647 B2 | 11/2016 | Van Zon et al. |
| 9,494,598 B2 | 11/2016 | Goix et al. |
| 9,518,984 B2 | 12/2016 | Graham et al. |
| 9,557,328 B2 | 1/2017 | Dittmer et al. |
| 9,575,081 B2 | 2/2017 | Nieuwenhuis et al. |
| 9,588,112 B2 | 3/2017 | Evers |
| 9,603,544 B2 | 3/2017 | Gleich |
| 9,612,236 B2 | 4/2017 | Sabatte et al. |
| 9,658,219 B2 | 5/2017 | Verschuren et al. |
| 10,036,757 B2 | 7/2018 | Singh et al. |
| 10,048,257 B2 | 8/2018 | Mak et al. |
| 10,227,639 B2 | 3/2019 | Levner et al. |
| 10,261,076 B2 | 4/2019 | Shultz et al. |
| 10,274,501 B2 | 4/2019 | Yin et al. |
| 10,376,881 B2 | 8/2019 | Lowe et al. |
| 10,386,364 B2 | 8/2019 | Lee et al. |
| 10,488,408 B2 | 11/2019 | Van Der Wijk et al. |
| 10,527,614 B2 | 1/2020 | Peretz |
| 2001/0049111 A1 | 12/2001 | Windhab et al. |
| 2002/0009738 A1 | 1/2002 | Houghton et al. |
| 2002/0028519 A1 | 3/2002 | Yguerabide et al. |
| 2002/0045276 A1 | 4/2002 | Yguerabide et al. |
| 2002/0058019 A1 | 5/2002 | Berenson et al. |
| 2002/0076154 A1 | 6/2002 | Maisenhoelder et al. |
| 2002/0094548 A1 | 7/2002 | Feistel |
| 2002/0106314 A1 | 8/2002 | Pelrine et al. |
| 2002/0119447 A1 | 8/2002 | Simons et al. |
| 2002/0123134 A1 | 9/2002 | Huang et al. |
| 2002/0136668 A1 | 9/2002 | Wallace et al. |
| 2002/0160363 A1 | 10/2002 | McDevitt et al. |
| 2002/0168663 A1 | 11/2002 | Phan et al. |
| 2002/0172987 A1 | 11/2002 | Terstappen et al. |
| 2002/0177144 A1 | 11/2002 | Remacle et al. |
| 2002/0197645 A1 | 12/2002 | Martin |
| 2003/0040129 A1 | 2/2003 | Shah |
| 2003/0042048 A1 | 3/2003 | Hughes et al. |
| 2003/0066956 A1 | 4/2003 | Gruber et al. |
| 2003/0092090 A1 | 5/2003 | Hajizadeh et al. |

(56) References Cited

U.S. PATENT DOCUMENTS

| | | |
|---|---|---|
| 2003/0094369 A1 | 5/2003 | Tolley et al. |
| 2003/0124592 A1 | 7/2003 | Puskas |
| 2003/0129749 A1 | 7/2003 | Gundersen et al. |
| 2003/0134416 A1 | 7/2003 | Yamanishi et al. |
| 2003/0142901 A1 | 7/2003 | Lahann et al. |
| 2003/0157327 A1 | 8/2003 | Barbera-Guillem et al. |
| 2003/0157731 A1 | 8/2003 | Yguerabide et al. |
| 2003/0170631 A1 | 9/2003 | Houghton et al. |
| 2003/0186323 A1 | 10/2003 | Vogel et al. |
| 2003/0207328 A1 | 11/2003 | Yguerabide et al. |
| 2004/0005723 A1 | 1/2004 | Empedocles et al. |
| 2004/0009614 A1 | 1/2004 | Ahn et al. |
| 2004/0018519 A1 | 1/2004 | Wright, Jr. |
| 2004/0043507 A1 | 3/2004 | Song et al. |
| 2004/0043509 A1 | 3/2004 | Stalher et al. |
| 2004/0058389 A1 | 3/2004 | Wang et al. |
| 2004/0137430 A1 | 7/2004 | Anderson et al. |
| 2004/0142463 A1 | 7/2004 | Walker et al. |
| 2004/0147031 A1 | 7/2004 | Nakao |
| 2004/0157271 A1 | 8/2004 | Kirakossian et al. |
| 2004/0166514 A1 | 8/2004 | Puskas |
| 2004/0166553 A1 | 8/2004 | Nguyen et al. |
| 2004/0181343 A1 | 9/2004 | Wigstrom et al. |
| 2004/0219580 A1 | 11/2004 | Dunn et al. |
| 2004/0253632 A1 | 12/2004 | Rhode et al. |
| 2004/0256157 A1 | 12/2004 | Tessari et al. |
| 2005/0003346 A1 | 1/2005 | Voorhees et al. |
| 2005/0003559 A1 | 1/2005 | Weber et al. |
| 2005/0064395 A1 | 3/2005 | Israel et al. |
| 2005/0074774 A1 | 4/2005 | Woudenberg et al. |
| 2005/0079598 A1 | 4/2005 | Davis |
| 2005/0129727 A1 | 6/2005 | Weber et al. |
| 2005/0158723 A1 | 7/2005 | Viovy et al. |
| 2005/0164205 A1 | 7/2005 | Puskas |
| 2005/0222504 A1 | 10/2005 | Otvos et al. |
| 2005/0232929 A1 | 10/2005 | Kadkhodayan et al. |
| 2005/0239108 A1 | 10/2005 | Barletta et al. |
| 2005/0244850 A1 | 11/2005 | Huang et al. |
| 2005/0250220 A1 | 11/2005 | Kozulic |
| 2005/0255464 A1 | 11/2005 | Hagen et al. |
| 2005/0261479 A1 | 11/2005 | Hoffmann et al. |
| 2005/0266417 A1 | 12/2005 | Barany et al. |
| 2005/0272110 A1 | 12/2005 | Drukier |
| 2006/0003333 A1 | 1/2006 | Puskas |
| 2006/0008206 A1 | 1/2006 | Maisenholder et al. |
| 2006/0024722 A1 | 2/2006 | Fischer-Colbrie et al. |
| 2006/0025713 A1 | 2/2006 | Rosengart et al. |
| 2006/0078998 A1 | 4/2006 | Puskas et al. |
| 2006/0131542 A1 | 6/2006 | Weng et al. |
| 2006/0177882 A1 | 8/2006 | Talebpour et al. |
| 2006/0194327 A1 | 8/2006 | Kahlan et al. |
| 2006/0199273 A1 | 9/2006 | Rabe et al. |
| 2006/0210987 A1 | 9/2006 | Gleich |
| 2006/0216238 A1 | 9/2006 | Manchester et al. |
| 2006/0263832 A1 | 11/2006 | Shang et al. |
| 2006/0281102 A1 | 12/2006 | Puskas |
| 2007/0003528 A1 | 1/2007 | Consigny et al. |
| 2007/0020620 A1 | 1/2007 | Finn et al. |
| 2007/0020649 A1 | 1/2007 | Tseng et al. |
| 2007/0116682 A1 | 5/2007 | Atala et al. |
| 2007/0116683 A1 | 5/2007 | Atala et al. |
| 2007/0116684 A1 | 5/2007 | Atala et al. |
| 2007/0161121 A1 | 7/2007 | Schuchard et al. |
| 2007/0161124 A1 | 7/2007 | Schuchard et al. |
| 2007/0166740 A1 | 7/2007 | Heil et al. |
| 2007/0166741 A1 | 7/2007 | Heil et al. |
| 2007/0191819 A1 | 8/2007 | Steinfeld et al. |
| 2007/0191963 A1 | 8/2007 | Winterbottom et al. |
| 2007/0231790 A1 | 10/2007 | Su |
| 2007/0275396 A1 | 11/2007 | Zheng |
| 2008/0011977 A1 | 1/2008 | Atwood |
| 2008/0021674 A1 | 1/2008 | Puskas |
| 2008/0039630 A1 | 2/2008 | Haugland et al. |
| 2008/0135490 A1 | 6/2008 | Li et al. |
| 2008/0139399 A1 | 6/2008 | Fonnum et al. |
| 2008/0158543 A1 | 7/2008 | Puskas et al. |
| 2008/0171352 A1 | 7/2008 | Goix et al. |
| 2008/0187472 A1 | 8/2008 | Ahn et al. |
| 2008/0196483 A1 | 8/2008 | Kurt et al. |
| 2008/0199851 A1 | 8/2008 | Egan et al. |
| 2008/0218165 A1 | 9/2008 | Kahlman et al. |
| 2008/0268481 A1 | 10/2008 | Prins et al. |
| 2008/0269069 A1 | 10/2008 | Bacher et al. |
| 2008/0272516 A1 | 11/2008 | Liu et al. |
| 2008/0280285 A1 | 11/2008 | Chen et al. |
| 2008/0305489 A1 | 12/2008 | Thomas et al. |
| 2008/0309329 A1 | 12/2008 | Kahlman et al. |
| 2008/0314749 A1 | 12/2008 | Johnson et al. |
| 2009/0028910 A1 | 1/2009 | DeSimone et al. |
| 2009/0029478 A1 | 1/2009 | Puskas |
| 2009/0054262 A1 | 2/2009 | Abbott et al. |
| 2009/0081711 A1 | 3/2009 | Singh |
| 2009/0087860 A1 | 4/2009 | Todd et al. |
| 2009/0087862 A1 | 4/2009 | Carter et al. |
| 2009/0088982 A1 | 4/2009 | Fukushima et al. |
| 2009/0102472 A1 | 4/2009 | Nieuwenhhuis et al. |
| 2009/0105087 A1 | 4/2009 | Kahlman et al. |
| 2009/0117168 A1 | 5/2009 | Keenan |
| 2009/0117670 A1 | 5/2009 | Van Der Wijk et al. |
| 2009/0142772 A1 | 6/2009 | Lau et al. |
| 2009/0148869 A1 | 6/2009 | Zaugg et al. |
| 2009/0156422 A1 | 6/2009 | Punyadeera et al. |
| 2009/0156423 A1 | 6/2009 | Stahler et al. |
| 2009/0156428 A1 | 6/2009 | Malcolm |
| 2009/0170212 A1 | 7/2009 | Van Der Wijk et al. |
| 2009/0171590 A1 | 7/2009 | Puskas et al. |
| 2009/0181402 A1 | 7/2009 | Finn et al. |
| 2009/0186420 A1 | 7/2009 | Kahlman et al. |
| 2009/0214618 A1 | 8/2009 | Schoenfisch et al. |
| 2009/0216170 A1 | 8/2009 | Robinson et al. |
| 2009/0219012 A1 | 9/2009 | Nieuwenhuis et al. |
| 2009/0234202 A1 | 9/2009 | Goix et al. |
| 2009/0253215 A1 | 10/2009 | Hikmet et al. |
| 2009/0269858 A1 | 10/2009 | Punyadeera et al. |
| 2009/0275031 A1 | 11/2009 | Tanner et al. |
| 2009/0280571 A1 | 11/2009 | Nieuwenhuis et al. |
| 2009/0301885 A1 | 12/2009 | Guzman |
| 2009/0305290 A1 | 12/2009 | Sambursky et al. |
| 2009/0325164 A1 | 12/2009 | Vossenaar et al. |
| 2010/0022857 A1 | 1/2010 | Ergeneman et al. |
| 2010/0087327 A1 | 4/2010 | Weng et al. |
| 2010/0112727 A1 | 5/2010 | Todd et al. |
| 2010/0152651 A1 | 6/2010 | Boyden et al. |
| 2010/0159445 A1 | 6/2010 | Lustig et al. |
| 2010/0194386 A1 | 8/2010 | Prins et al. |
| 2010/0221842 A1 | 9/2010 | Klumder et al. |
| 2010/0248973 A1 | 9/2010 | Van Lankvelt et al. |
| 2010/0255518 A1 | 10/2010 | Goix et al. |
| 2010/0261195 A1 | 10/2010 | Rubenstein et al. |
| 2010/0267165 A1 | 10/2010 | Bruls et al. |
| 2010/0272608 A1 | 10/2010 | Penterman et al. |
| 2010/0273142 A1 | 10/2010 | Prins et al. |
| 2010/0273269 A1 | 10/2010 | Van Lankvelt et al. |
| 2010/0285490 A1 | 11/2010 | Dees et al. |
| 2010/0285606 A1 | 11/2010 | Phillips et al. |
| 2010/0297780 A1 | 11/2010 | De Theije et al. |
| 2010/0311085 A1 | 12/2010 | Zaugg et al. |
| 2010/0322824 A1 | 12/2010 | Neijzen |
| 2010/0323355 A1 | 12/2010 | Dittmer |
| 2011/0020836 A1 | 1/2011 | Li |
| 2011/0033522 A1 | 2/2011 | Reinherz et al. |
| 2011/0045470 A1 | 2/2011 | Murakami et al. |
| 2011/0059547 A1 | 3/2011 | Dehal et al. |
| 2011/0065209 A1 | 3/2011 | Heil et al. |
| 2011/0091903 A1 | 4/2011 | Bommarito et al. |
| 2011/0107855 A1 | 5/2011 | Motadel |
| 2011/0111428 A1 | 5/2011 | Carter et al. |
| 2011/0117202 A1 | 5/2011 | Bourke, Jr. et al. |
| 2011/0117668 A1 | 5/2011 | Stayton et al. |
| 2011/0136099 A1 | 6/2011 | Schneider et al. |
| 2011/0206560 A1 | 8/2011 | Neijzen et al. |
| 2011/0207150 A1 | 8/2011 | Zaugg et al. |
| 2011/0207171 A1 | 8/2011 | Agnew et al. |
| 2011/0208040 A1 | 8/2011 | Carmi et al. |

(56) References Cited

U.S. PATENT DOCUMENTS

| | | |
|---|---|---|
| 2011/0235037 A1 | 9/2011 | Schleipen |
| 2011/0237704 A1 | 9/2011 | Guelcher et al. |
| 2011/0244594 A1 | 10/2011 | Horii |
| 2011/0256640 A1 | 10/2011 | Dittmer et al. |
| 2011/0301053 A1 | 12/2011 | Todd et al. |
| 2012/0019240 A1 | 1/2012 | Müller et al. |
| 2012/0031773 A1 | 2/2012 | Miller |
| 2012/0034633 A1 | 2/2012 | Miller et al. |
| 2012/0034684 A1 | 2/2012 | Emerson et al. |
| 2012/0062219 A1 | 3/2012 | Craus |
| 2012/0082728 A1 | 4/2012 | Schneider et al. |
| 2012/0100546 A1 | 4/2012 | Lowery, Jr. et al. |
| 2012/0119727 A1 | 5/2012 | Prins et al. |
| 2012/0135530 A1 | 5/2012 | Bamdad et al. |
| 2012/0149128 A1 | 6/2012 | Manneh |
| 2012/0156693 A1 | 6/2012 | Wong et al. |
| 2012/0171781 A1 | 7/2012 | Dittmer et al. |
| 2012/0178186 A1 | 7/2012 | Nieuwenhuis et al. |
| 2012/0181176 A1 | 7/2012 | Atwood |
| 2012/0184046 A1 | 7/2012 | Atkin |
| 2012/0208296 A1 | 8/2012 | Ranzoni et al. |
| 2012/0212733 A1 | 8/2012 | Kodali et al. |
| 2012/0220051 A1 | 8/2012 | Yin et al. |
| 2012/0230911 A1 | 9/2012 | Hsieh et al. |
| 2012/0258126 A1 | 10/2012 | Schøller et al. |
| 2012/0262565 A1 | 10/2012 | Kahlman et al. |
| 2012/0264133 A1 | 10/2012 | Sambursky et al. |
| 2012/0282636 A1 | 11/2012 | Altschul et al. |
| 2013/0034527 A1 | 2/2013 | Hyde et al. |
| 2013/0088221 A1 | 4/2013 | Van Zon et al. |
| 2013/0109030 A1 | 5/2013 | Hardeman et al. |
| 2013/0109106 A1 | 5/2013 | Klunder et al. |
| 2013/0122492 A1 | 5/2013 | Khosravi et al. |
| 2013/0137117 A1 | 5/2013 | Levi et al. |
| 2013/0196341 A1 | 8/2013 | Neely et al. |
| 2013/0214040 A1 | 8/2013 | Beerling et al. |
| 2013/0260367 A1 | 10/2013 | Lowery, Jr. et al. |
| 2013/0260390 A1 | 10/2013 | Goix et al. |
| 2013/0266930 A1 | 10/2013 | Dinges |
| 2013/0267039 A1 | 10/2013 | Todd et al. |
| 2013/0267431 A1 | 10/2013 | Singh et al. |
| 2013/0315783 A1 | 11/2013 | Carter et al. |
| 2013/0316468 A1 | 11/2013 | Todd et al. |
| 2014/0051070 A1 | 2/2014 | Arai et al. |
| 2014/0057366 A1 | 2/2014 | Dittmer et al. |
| 2014/0065616 A1 | 3/2014 | Xu |
| 2014/0094383 A1 | 4/2014 | Lee et al. |
| 2014/0100102 A1 | 4/2014 | Rajagopal et al. |
| 2014/0120632 A1 | 5/2014 | Ranzoni et al. |
| 2014/0127713 A1 | 5/2014 | De Theije et al. |
| 2014/0127722 A1 | 5/2014 | Ranzoni et al. |
| 2014/0147932 A1 | 5/2014 | Goix et al. |
| 2014/0154257 A1 | 6/2014 | DeChristopher |
| 2014/0170652 A1 | 6/2014 | Sitdikov et al. |
| 2014/0170767 A1 | 6/2014 | Lee et al. |
| 2014/0179025 A1 | 6/2014 | Weng et al. |
| 2014/0186940 A1 | 7/2014 | Goel |
| 2014/0193488 A1 | 7/2014 | Kim et al. |
| 2014/0205996 A1 | 7/2014 | Lizzi et al. |
| 2014/0206632 A1 | 7/2014 | Todd et al. |
| 2014/0227715 A1 | 8/2014 | Todd et al. |
| 2014/0251832 A1 | 9/2014 | Porter |
| 2014/0274762 A1 | 9/2014 | Manuguerra et al. |
| 2014/0295420 A1 | 10/2014 | Ovsyanko et al. |
| 2014/0295432 A1 | 10/2014 | Evers et al. |
| 2014/0302535 A1 | 10/2014 | Lovell et al. |
| 2014/0308680 A1 | 10/2014 | Van Lieshout |
| 2014/0328999 A1 | 11/2014 | Aizenberg et al. |
| 2014/0330257 A1 | 11/2014 | Hyde et al. |
| 2014/0335527 A1 | 11/2014 | Goel |
| 2014/0342468 A1 | 11/2014 | Todd et al. |
| 2014/0363833 A1 | 12/2014 | Bhatia et al. |
| 2014/0377771 A1 | 12/2014 | Bibette et al. |
| 2014/0377789 A1 | 12/2014 | Moerman |
| 2014/0377837 A1 | 12/2014 | Agnew et al. |
| 2015/0024974 A1 | 1/2015 | Banerjee et al. |
| 2015/0072396 A1 | 3/2015 | Gee et al. |
| 2015/0093750 A1 | 4/2015 | Ovsyanko et al. |
| 2015/0105284 A1 | 4/2015 | Willson et al. |
| 2015/0119275 A1 | 4/2015 | Todd et al. |
| 2015/0140684 A1 | 5/2015 | Kim et al. |
| 2015/0141259 A1 | 5/2015 | Sanders et al. |
| 2015/0160217 A1 | 6/2015 | Wong et al. |
| 2015/0165092 A1 | 6/2015 | Kaplan et al. |
| 2015/0168390 A1 | 6/2015 | Maas et al. |
| 2015/0177239 A1 | 6/2015 | Evers et al. |
| 2015/0187479 A1 | 7/2015 | Van Lieshout et al. |
| 2015/0198532 A1 | 7/2015 | Lee et al. |
| 2015/0226732 A1 | 8/2015 | De Theije et al. |
| 2015/0233908 A1 | 8/2015 | Kelly et al. |
| 2015/0299764 A1 | 10/2015 | Raspe et al. |
| 2015/0316545 A1 | 11/2015 | Peck et al. |
| 2015/0316549 A2 | 11/2015 | Feldman et al. |
| 2015/0323523 A1 | 11/2015 | Evers et al. |
| 2015/0329617 A1 | 11/2015 | Winther et al. |
| 2016/0003814 A1 | 1/2016 | Hamasaki et al. |
| 2016/0008788 A1 | 1/2016 | Nassar |
| 2016/0010136 A1 | 1/2016 | Nassar |
| 2016/0041166 A1 | 2/2016 | Jablonski et al. |
| 2016/0054311 A1 | 2/2016 | Marks et al. |
| 2016/0061826 A1 | 3/2016 | Sohn et al. |
| 2016/0084762 A1 | 3/2016 | Goix et al. |
| 2016/0091497 A1 | 3/2016 | Goix et al. |
| 2016/0123965 A1 | 5/2016 | Evers et al. |
| 2016/0178520 A1 | 6/2016 | Livingston |
| 2016/0186253 A1 | 6/2016 | Talasaz et al. |
| 2016/0195524 A1 | 7/2016 | Cowan et al. |
| 2016/0202248 A1 | 7/2016 | Lee et al. |
| 2016/0202270 A1 | 7/2016 | Goix et al. |
| 2016/0216256 A1 | 7/2016 | Miller et al. |
| 2016/0223530 A1 | 8/2016 | Marshall et al. |
| 2016/0237478 A1 | 8/2016 | Jewett et al. |
| 2016/0250612 A1 | 9/2016 | Oldenburg et al. |
| 2016/0266041 A1 | 9/2016 | Livingston |
| 2016/0291004 A1 | 10/2016 | Sijbers et al. |
| 2016/0319341 A1 | 11/2016 | Dressman et al. |
| 2017/0000899 A1 | 1/2017 | Pridgen et al. |
| 2017/0016890 A1 | 1/2017 | Giehring |
| 2017/0022546 A1 | 1/2017 | Bashir et al. |
| 2017/0023593 A1 | 1/2017 | Van Roosmalen |
| 2017/0067889 A1 | 3/2017 | Tamir |
| 2017/0113223 A1 | 4/2017 | Immink et al. |
| 2017/0153248 A1 | 6/2017 | Goix et al. |
| 2018/0164297 A1 | 6/2018 | Post |
| 2018/0164305 A1 | 6/2018 | Hu et al. |
| 2018/0224444 A1 | 8/2018 | Sanders et al. |
| 2018/0321254 A1 | 11/2018 | Singh et al. |
| 2019/0033305 A1 | 1/2019 | Miller |
| 2019/0112641 A1 | 4/2019 | Celedon et al. |
| 2019/0154671 A1 | 5/2019 | Van Roosmalen et al. |
| 2019/0169689 A1 | 6/2019 | Zhu et al. |
| 2020/0041518 A1 | 2/2020 | Mei et al. |

FOREIGN PATENT DOCUMENTS

| | | |
|---|---|---|
| EP | 2629095 A1 | 8/2013 |
| EP | 2437048 B1 | 1/2016 |
| WO | WO 2007/122393 A1 | 11/2007 |
| WO | WO 2013/189502 A1 | 12/2013 |
| WO | WO 2015/135840 A1 | 9/2015 |
| WO | 2017/024163 A1 | 2/2017 |
| WO | WO 2018/023088 A1 | 2/2018 |
| WO | WO 2018/119437 A2 | 6/2018 |
| WO | WO 2018/140719 A1 | 8/2018 |
| WO | WO 2022/029731 A1 | 2/2022 |

OTHER PUBLICATIONS

Agrawal, et al., "Single-Bead Immunoassays Using Magnetic Microparticles and Spectral-Shifting Quantum Dots", Journal of Agricultural and Food Chemistry, vol. 55, pp. 3778-3782. 2007.

(56)  References Cited

OTHER PUBLICATIONS

Hsieh, et al., "Rapid and Sensitive Detection of Cancer Cells by Coupling with Quantum Dot and Immunomagnetic Separation at Low Concentrations", Biosensors and Bioelectronics, vol. 26, pp. 4249-4252. 2011.

International Search Report & Written Opinion, PCT Application No. PCT/US18/15440, dated Apr. 17, 2018, 14 pages.

Kim, et al., "Magnetic Bead-Quantum Dot Assay for Detection of a Biomarker for Traumatic Brain Injury", Nanoscale, vol. 7, pp. 17820-17826. 2015.

Motozawa, et al., "Effect of External Magnetic Field on Ultrasonic Propagation Velocity in Magentic Fluids," JSME International Journal, Series B, vol. 48, No. 3, pp. 471-477, 2005.

Oh, et al., "A Three-Linelateral Floe Assay Strip for The Measurement of C-Reactive Protein Covering a Broad Physiological Concentration Range in Human Sera", 2014, Biosenors and Bioelectronics, vol. 61, pp. 285-289. 2014.

Pi, et al., "A Sandwich Immunoassay for Detection of AB-42 Based on Quantum Dots", Talanta, vol. 146, pp. 10-15. 2016.

Wang, et al., "Rapid, Sensitive, and Simultaneous Detection of Three Foodborne Pathogens Using Magnetic Nanobead-Based Immunoseparation and Quantum Dot-Based Multiplex Immunoassay", Journal of Food Protection, vol. 74(12), pp. 2039-2047, 2011.

FIG. 1C
FIG. 1D
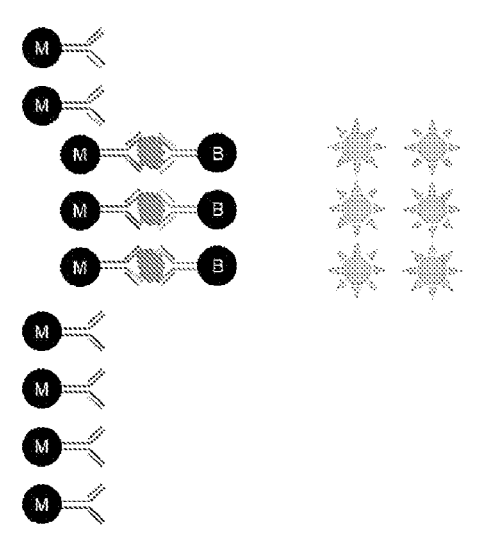
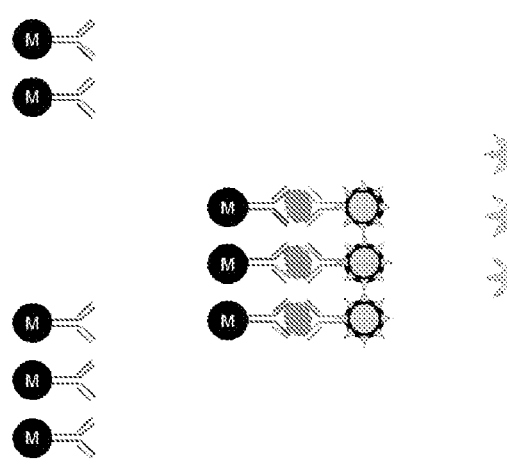
FIG. 1E
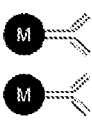
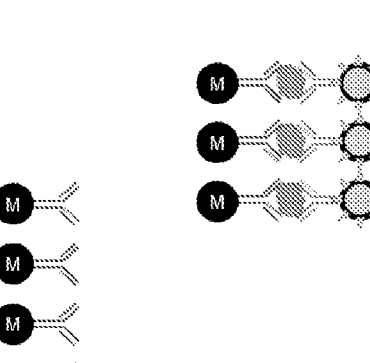

| LH system Blank sample 705-SA Reporter | | | |
|---|---|---|---|
| | Rep 1 | Rep 2 | Rep 3 | AVG |
| 20 pM | 12,248 | 36,501 | 6,074 | 18,274 |
| 200 pM | 156,741 | 194,765 | 179,397 | 176,968 |
| 1000 pM | 1,347,645 | 1,013,801 | 1,236,583 | 1,199,343 |
| 2000 pM | 4,888,647 | 4,815,180 | 5,185,784 | 4,963,204 |

Concentration-Dependent Background of Reporter

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 1

Gly Ala Pro Val Pro Tyr Pro Asp Pro Leu Glu Pro Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 2

Asp Tyr Lys Asp Asp Asp Asp Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 3

Glu Gln Lys Leu Ile Ser Glu Glu Asp Leu
1               5                   10
```

-continued

```
<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 4

Tyr Pro Tyr Asp Val Pro Asp Tyr Ala
1               5
```

KINETIC MODULATION FOR MAGNETIC ANALYTE DETECTION

CROSS-REFERENCE TO RELATED APPLICATIONS

This application is a National Stage Entry of PCT/IB2021/057295, filed Aug. 7, 2021, which claims the benefit of U.S. Provisional Patent Application No. 63/063,029 filed Aug. 7, 2020 entitled "KINETIC MODULATION FOR MAGNETIC ANALYTE DETECTION," which is incorporated by reference herein in its entirety.

TECHNICAL FIELD

The present invention relates to, inter alia, methods to detect presence, absence, or amount of an analyte in a biological sample with improved kinetics of the detection.

SEQUENCE LISTING

This instant application contains a Sequence Listing that has been submitted in XML format via EFS-Web and is hereby incorporated by reference in its entirety. Said XML copy, created on Feb. 2, 2023, is named 124436-5012 Sequence Listing.xml and is 6,089 bytes in size.

BACKGROUND

To diagnose diseases and conditions, monitor and assess treatment progression, and to perform various other healthcare-related tasks, reliable tests are often required to detect and quantify a diverse range of targets, including but not limited to proteins, bacteria, whole cells, viruses, and small molecules.

Analyte detection has various clinical and non-clinical applications in industries ranging from medicine and biological research to environmental science and beyond. Traditional methods for analyte detection involve assays such as enzyme-linked immunosorbent assays (ELISA), mass spectrometry, and high pressure liquid chromatography (HPLC). While HPLC and mass spectrometry may be used to detect analytes on the basis of charge and/or size, ELISA may be used to detect an analyte based on antigens on the analyte that are recognizable by capture and detection agents (e.g., antibodies, aptamers, etc.). In particular, ELISA assay has become a common detection method. However, conventional ELISA may be time-consuming as it involves various incubation and washing steps. Also, parameters for carrying out ELISA assays are highly variable, and traditional ELISA platforms may not provide adequate sensitivity and specificity.

Various diagnostic methods have been developed to detect antibodies and antigens, including ELISA, agglutination, precipitation, complement-fixation, fluorescent antibodies, and chemiluminescence. For example, serological tests are diagnostic methods that are used to identify antibodies and antigens in a patient's sample. The knowledge of a serological status of a person regarding a certain infectious disease, autoimmune disease, allergy, etc. is useful for various applications, including diagnosis, selection of treatment, monitoring of treatment, establishing of quarantine, making decisions in forensics, biometric identification, etc. Serological tests can also be applied to determining a person's blood type.

Each of the existing approaches has its advantages and drawbacks, and problems that remain to be solved relate to the reliability, speed, and cost of the testing. Also, conventional immunoassays may have long processing times and often less than desirable sensitivity and specificity. The prolonged time required to perform an analyte detection using a conventional approach can be a significant limitation for many clinical applications where it is desired to process samples promptly. Decreased samples analysis times may be critical for epidemiological applications. For example, as the COVID-19 (SARS-COV-2 or 2019-nCOV) pandemic has shown, quick and reliable processing of large number of samples can be a life-saving approach for identifying infected subjects, for contact tracing, and for ultimate return to normal.

Accordingly, there exist a need for quick and accurate diagnostic tests for comprehensive analysis of a biological sample.

SUMMARY

Accordingly, in various aspects, the present invention provides methods for detecting the presence, absence, or amount of an analyte in a biological sample, or kits to effect such methods. The method allows for detection of one or more analytes in a sample with greatly improved kinetics such that an entire assay in accordance with embodiments of the present disclosure can be performed in a range from about 1 minute to about 20 minutes. For comparison, traditional assays require from about 1.5 hours to about 6 hours.

In embodiments, a method for detecting the presence, absence, or amount of an analyte in a biological sample is provided. The method comprises (a) contacting the sample with a magnetic conjugate comprising a magnetic particle and a capture moiety configured to bind an analyte in the sample; (b) contacting the magnetic conjugate with a reporter binding moiety having a tag bound thereto, the reporter binding moiety being configured to bind the analyte; (c) contacting the magnetic conjugate with a reporter having a tag binding partner that is configured to bind the tag thereby optionally associating a reporter binding moiety bound to the tag with the reporter, wherein a concentration of the reporter binding moiety is substantially greater than a concentration of the reporter; (d) applying a magnetic field to separate the magnetic conjugate, optionally having an analyte that has the reporter binding moiety associated with the reporter bound thereto; and (e) detecting the presence, absence, or level of the analyte based on detection of a signal generated by the reporter. The reporter can be detected in various ways, depending on a type of the reporter.

In some embodiments, the method for detecting the presence, absence, or amount of an analyte in a biological sample comprises (a) contacting the sample with a magnetic conjugate comprising a magnetic particle and a capture moiety configured to bind an analyte in the sample; (b) contacting the sample with a reporter binding moiety having a tag bound thereto, the reporter binding moiety being configured to bind the analyte; (c) contacting the sample with a reporter having a tag binding partner bound thereto such that the tag binding partner binds the tag thereby associating a reporter binding moiety bound to the tag with the reporter, wherein a concentration of the reporter binding moiety is substantially greater than a concentration of the reporter; (d) separating the analyte that has the magnetic conjugate and the reporter binding moiety associated with the reporter bound thereto via a tag-tag binding partner interaction from the sample by applying a magnetic field; and (e) detecting the presence, absence, or level of the analyte based on detection of a signal generated by the reporter.

In embodiments of the present disclosure, instead of using a reporter conjugate (i.e. a reporter binding moiety with a reporter bound thereto) like in conventional immunoassays, a reporter binding moiety has a tag bound thereto rather than a reporter. The reporter binding moiety interacts with the reporter via an interaction between a tag bound to that reporter binding moiety and a corresponding tag binding partner bound to the reporter. This system allows the use of an increased concentration of the reporter binding moiety that is substantially greater than a concentration of the reporter. Thus, in some embodiments, the concentration of the reporter binding moiety is at least about 5 times greater, or at least about 10 times greater, or at least about 100 times greater, or at least about 1000 times greater than the con-centration of the reporter. In some embodiments, the con-centration of the reporter binding moiety is about 1000 times greater than the concentration of the reporter.

In some embodiments, the concentration of the reporter is in a picomolar range. For example, the concentration of the reporter may be less than about 300 pM. In some embodi-ments, the concentration of the reporter is from about 10 pM to about 100 pM, optionally from about 40 pM to about 120 pM. In some embodiments, the concentration of the reporter is about 20 pM. In some embodiments, the concentration of the reporter is about 120 pM.

In some embodiments, the concentration of the reporter binding moiety is in a nanomolar range. For example, the concentration of the reporter binding moiety may be greater than about 1 nm. In some embodiments, the concentration of the reporter binding moiety is from about 1 nm to about 60 nM, or from about 1 nm to about 50 nM, or from about 1 nm to about 40 nM, or from about 1 nm to about 30 nM, or from about 1 nm to about 20 nM, or from about 1 nm to about 15 nM, or from about 1 nm to about 10 nM, or from about 1 nm to about 5 nM. In some embodiments, the concentration of the reporter binding moiety is from about 100 nm to about 800 nM (e.g., about 600 nM).

In some embodiments, the concentration of the reporter binding moiety ranges from about 1 nM to about 10 nM, and the concentration of the reporter ranges from about 15 pM to about 25 pM. In some embodiments, the concentration of the reporter binding moiety is about 5 nM and the concen-tration of the reporter is about 20 pM.

In some embodiments, the reporter comprises a metal core and a silica shell or the reporter; wherein the silica shell is optionally impregnated with a plurality of quantum dots; and wherein the metal core optionally comprises gold. The reporter may also comprise a plurality of quantum dots. In some embodiments, the reporter is a fluorescent reporter, a phosphorescent reporter, or a colorimetric reporter.

In some embodiments, the tag comprises biotin and the tag binding partner comprises streptavidin. Any other types of tags and tag binding partners can be used.

Embodiments of the present disclosure allow detecting various types of analytes. Thus, in some embodiments, the analyte is selected from the group consisting of human chorionic gonadotropin (hCG), luteinizing hormone (LH)/ Lutropin, prostate specific antigen (PSA), herpes simplex virus (HSV) antibodies, estrone-3-glucuronide (E3G), bac-teria, hemoglobin A1C, C-reactive protein (CRP), an inflam-mation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an: influenza virus biomarker, a liver function biomarker, estro-gen, progesterone, lactic acid, and combinations thereof.

The sample may be whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, and pus, or any other types of a sample.

In some embodiments, the analyte comprises an antibody, and the capture moiety of the magnetic conjugate comprises an antigen configured to bind the antibody. The reporter binding moiety may comprise a secondary antibody config-ured to bind the antigen. In some embodiments, the biologi-cal sample may be obtained from a subject, and the method indicates whether the subject is producing or not producing antibodies directed against an antigen. In some embodi-ments, the method provides an amount of antibodies in the sample.

In some embodiments, sensitivity of a method in accor-dance with embodiments of the present disclosure increases as the concentration of the reporter binding moiety increases and as the concentration of the reporter decreases.

The method in accordance with embodiments of the present disclosure provides various advantages as compared to a method using an assay in which a concentration of the reporter binding moiety is not substantially different from a concentration of the reporter. For example, in some embodi-ments, the method provides reduced background noise as compared to a method using an assay in which a concen-tration of the reporter binding moiety is not substantially different from a concentration of the reporter. In some embodiments, the method provides an increased signal-to-noise ratio as compared to a method using an assay in which a concentration of the reporter binding moiety is not sub-stantially different from a concentration of the reporter.

In some embodiments, the method provides better sensi-tivity and specificity than a method using an assay in which a concentration of the reporter binding moiety is not sub-stantially different from a concentration of the reporter.

In various aspects, the present invention provides a kit suitable for the method of any of the embodiments disclosed herein. The kit may comprise the magnetic conjugate, the reporter binding moiety, and the reporter.

The details of the invention are set forth in the accom-panying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Any aspect or embodiment disclosed herein can be com-bined with any other aspect or embodiment as disclosed herein.

BRIEF DESCRIPTION OF THE DRAWINGS

FIGS. 1A-1E depict schematically an example of an immunoassay in accordance with some embodiments of the present disclosure. FIG. 1A shows (left panel) components that are involved in the assay, and (right panel) magnetic particles each bound to a capture moiety (an antibody #1),

Figure 1A:
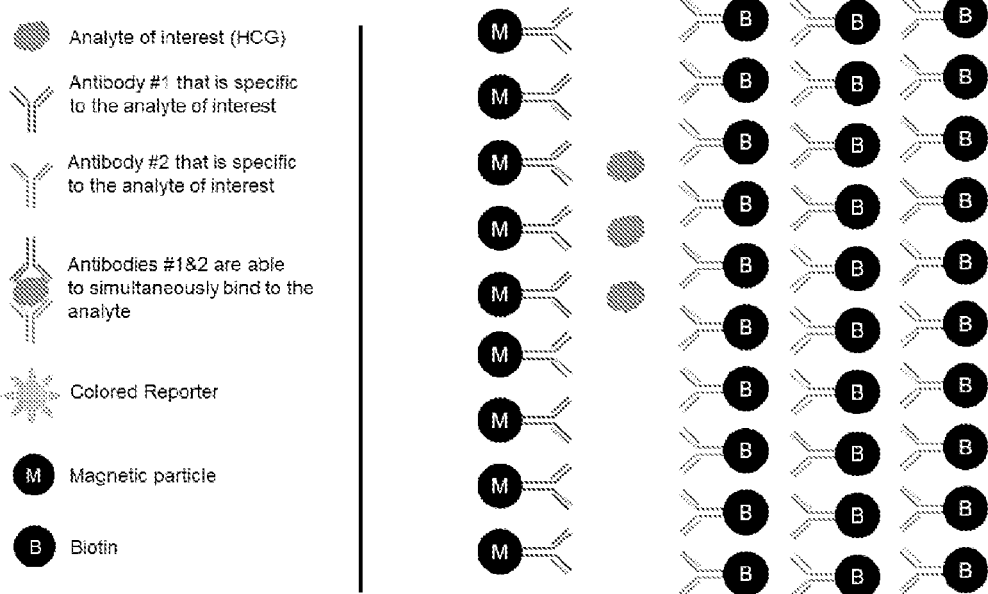
Figure 1B:
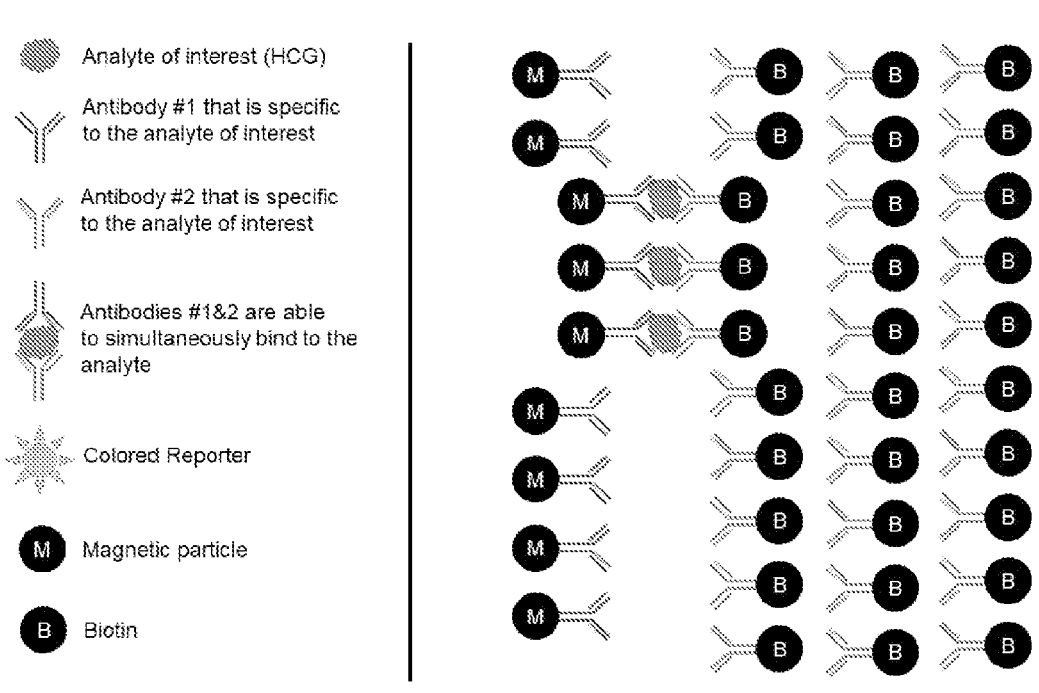

5 an analyte, and reporter binding moieties (an antibody #2) bound to a tag. FIG. 1B shows (left panel) components that are involved in the assay, and (right panel) that the antibodies #1 and #2 can simultaneously bind the analyte and that excess reporter binding moiety can be removed when a magnetic field is applied. FIG. 1C depicts that the sample can be resuspended with reporter particles. FIG. 1D shows that reporter particles added as shown in FIG. 1B each become associated with a reporter binding moiety to form a detectable complex. FIG. 1E illustrates that excess of the reporter particles is removed when a magnetic field is applied.

Figure 2:
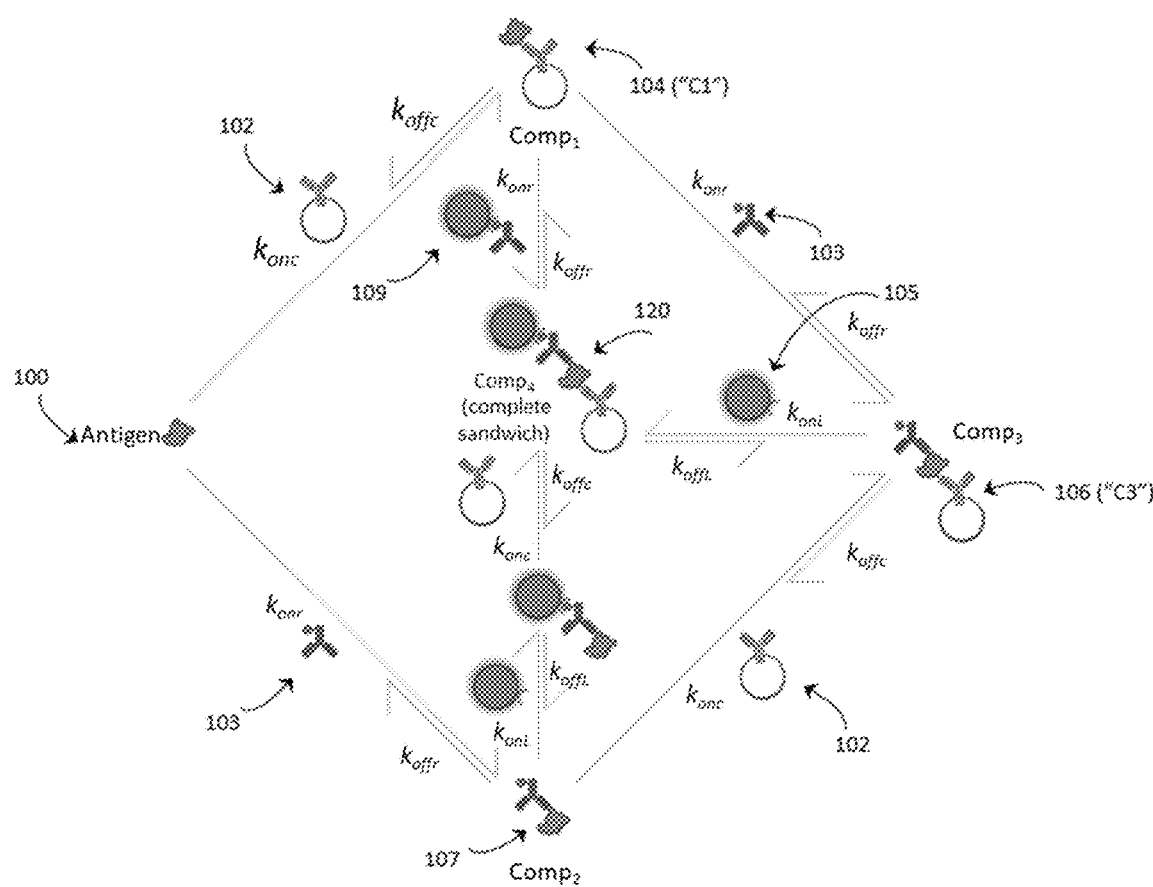

FIG. 2 is a schematic diagram illustrating an example of components, intermediate complexes, and a final complex formed in an immunoassay in accordance with some embodiments of the present disclosure.

Figure 3:
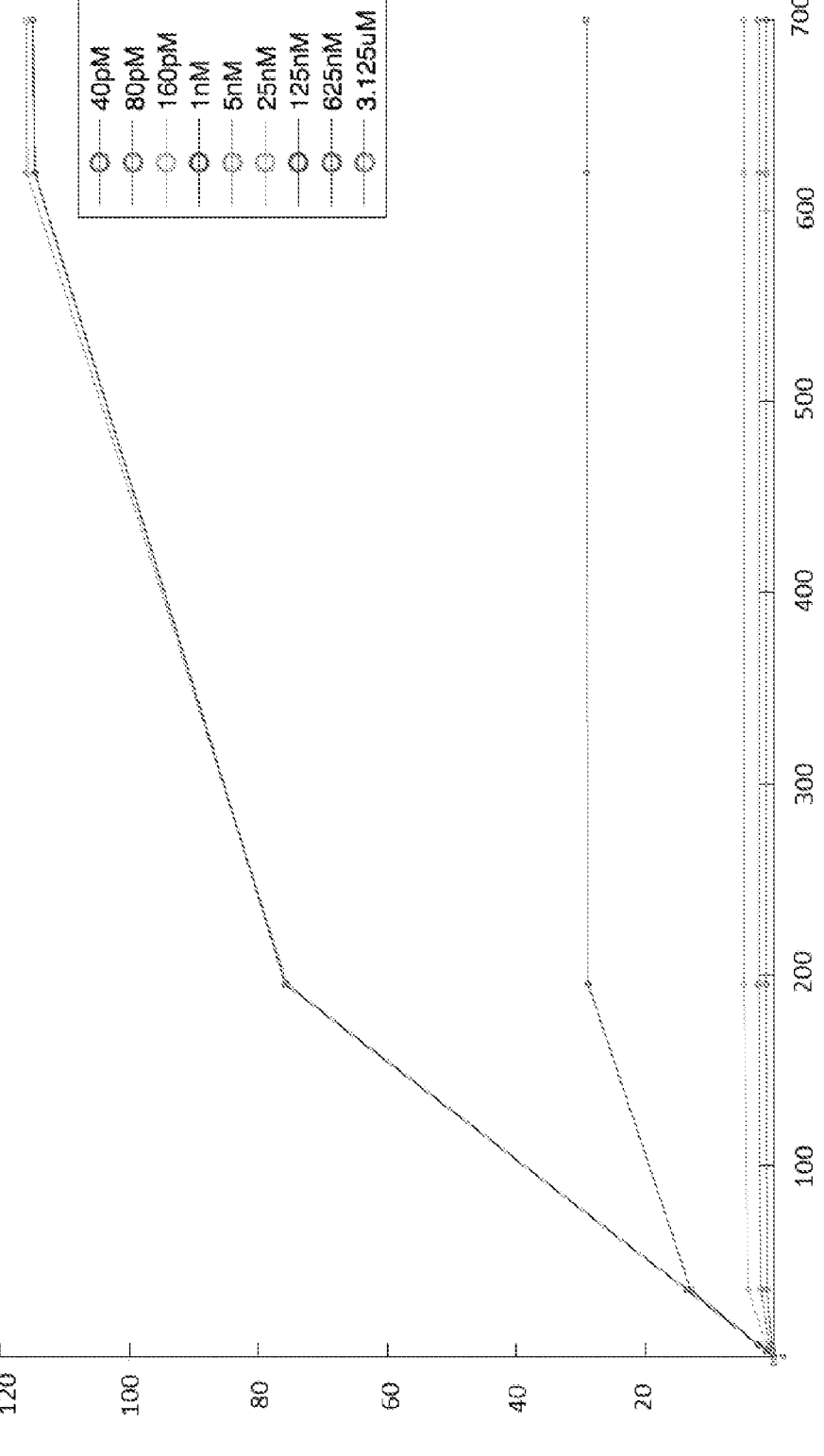

FIG. 3 is a graph showing results of a titration of a reporter binding moiety (Ab) with a tag in an assay in accordance with embodiments of the present disclosure, illustrating a resulting detected signal (Y-axis, in relative fluorescence units, MM) versus a concentration of an antibody of interest (hCG, in mIU/ml) (X-axis), for different concentrations of a reporter binding moiety (40 pM, 80 pM, 160 pM, 1 nM, 5 nM, 25 nM, 125 nM, 625 nM, and 3.125 uM).

Figure 4:
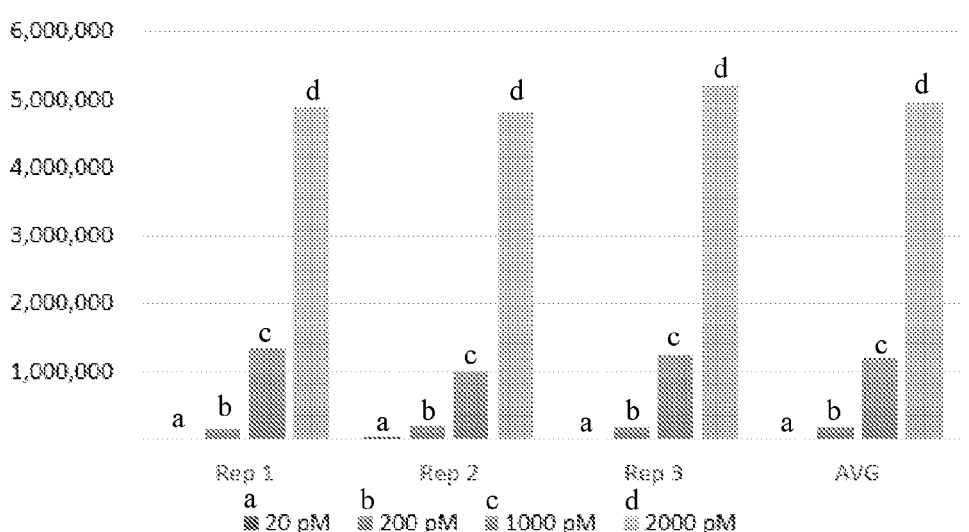

FIG. 4 is a graph showing results of a titration of the reporter in the assay, showing background noise in relative fluorescence units (MM) as it varies depending on a concentration of the reporter. For each of Rep 1, Rep 2, Rep 3, and AVG, there are four concentrations, left to right: 20 pM, 200 pM, 1000 pM, and 2000 pM.

Figure 5:
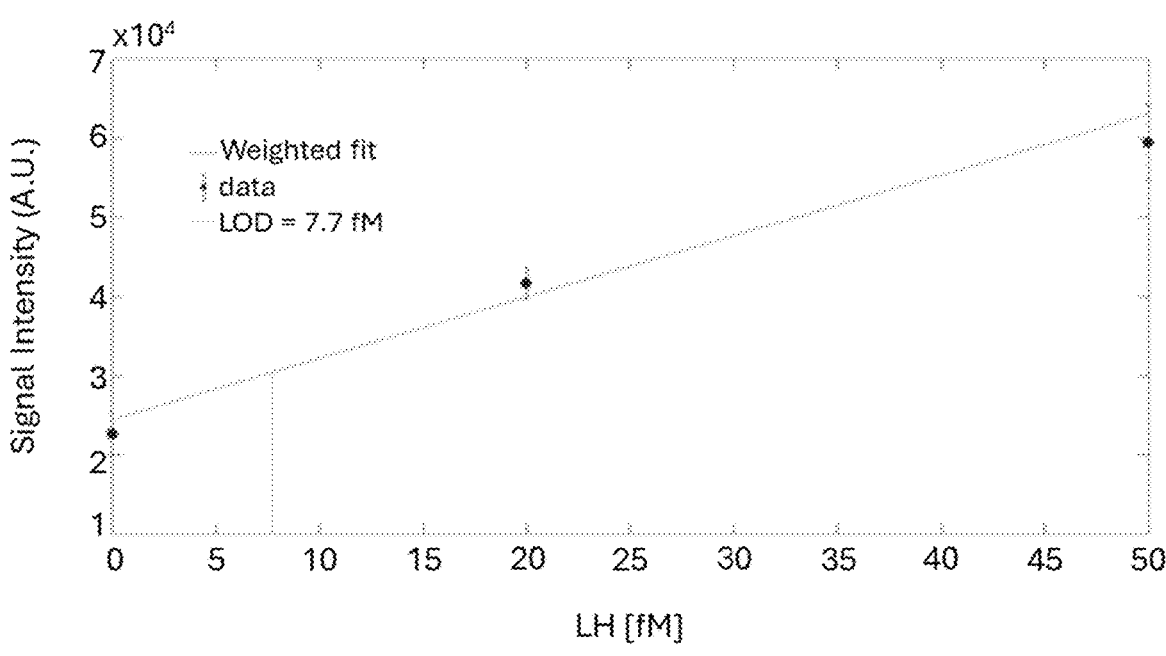

FIG. 5 is a graph showing the use of the present methods to achieve a limit of detection ("LOD") of 7.7 fM for luteinizing hormone ("LH") specific antibodies. Error bars represent the standard deviation of replicates.

Figure 6:
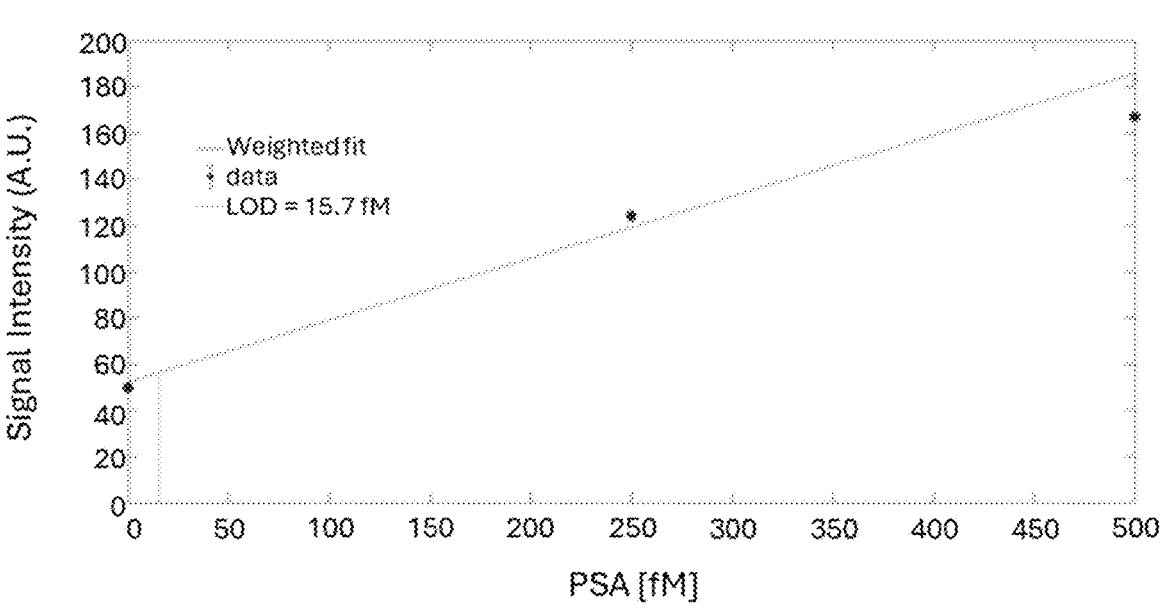

FIG. 6 is a graph showing the use of the present methods to achieve a limit of detection ("LOD") of 15.7 fM for prostate specific antigen ("PSA") specific antibodies. Error bars represent the standard deviation of replicates.

DETAILED DESCRIPTION

The present disclosure provides methods and systems that address the need for accurate detection of analytes in biological samples.

In various clinical and non-clinical applications related to diagnosing or treating a subject, it is desirable to detect an analyte in a sample quickly and accurately. However, conventional immunoassay often require a prolonged sample analysis time, which can be 6 hours or longer. Also, many conventional immunoassays not only take a relatively long time to detect an analyte, but also suffer from poor sensitivity (e.g., limit of detections (LoDs) in the picomolar-nanomolar range), poor sensitivity, and large sample volume requirements (e.g., hundreds of microliters).

Accordingly, embodiments of the present disclosure provide an immunoassay designed such that the kinetics of the detection is modulated. The described approach allows achieving significantly faster detection of an analyte—e.g. the detection may require from about 1 to about 20 minutes, on average about 15 minutes. In some embodiments, the immunoassay can be completed in as low as about 1 minute, or about 2 minutes, or about 3 minutes, or about 4, or about 5 minutes. Also, an immunoassay in accordance with embodiments of the present disclosure can have a low background across different samples (e.g., bodily fluids) and high sensitivity.

In various aspects, a method for detecting the presence, absence, or amount of an analyte in a biological sample is provided. In some embodiments, the method comprises (a) contacting the sample with a magnetic conjugate comprising a magnetic particle and a capture moiety configured to bind an analyte in the sample; (b) contacting the magnetic conjugate with a reporter binding moiety having a tag bound thereto, the reporter binding moiety being configured to bind the analyte; (c) contacting the magnetic conjugate with a reporter having a tag binding partner that is configured to bind the tag thereby optionally associating a reporter binding moiety bound to the tag with the reporter, wherein a concentration of the reporter binding moiety is substantially greater than a concentration of the reporter; (d) applying a magnetic field to separate the magnetic conjugate, optionally having an analyte that has the reporter binding moiety associated with the reporter bound thereto; and (e) detecting the presence, absence, or level of the analyte based on detection of a signal generated by the reporter.

The magnetic conjugate may have or not have an analyte associated therewith, which can be detected by detecting a signal generated by the reporter or by detecting the reporter, depending on whether or not the analyte is present in the sample. When an analyte is present in a biological sample, the magnetic conjugate can have associated therewith an analyte that has the reporter binding moiety associated with the reporter bound thereto. When the analyte is not present in a sample, the magnetic conjugate will not be associated with an analyte.

In some embodiments, the method comprises (a) contacting the sample with a magnetic conjugate comprising a magnetic particle and a capture moiety configured to bind an analyte in the sample; (b) contacting the sample with a reporter binding moiety having a tag bound thereto, the reporter binding moiety being configured to bind the analyte; and (c) contacting the sample with a reporter having a tag binding partner bound thereto such that the tag binding partner binds the tag thereby associating a reporter binding moiety bound to the tag with the reporter. A concentration of the reporter binding moiety is substantially greater than a concentration of the reporter. The method further comprises (d) separating the analyte that has the magnetic conjugate and the reporter binding moiety associated with the reporter bound thereto via a tag-tag binding partner interaction from the sample by applying a magnetic field, and (e) detecting the presence, absence, or level of the analyte based on detection of a signal generated by the reporter.

In the present method, a concentration of the reporter binding moiety is substantially greater than a concentration of the reporter. In some embodiments, the concentration of the reporter binding moiety is at least about 5 times greater, or at least about 10 times greater, or at least about 100 times greater, or at least about 1000 times greater than the concentration of the reporter. In some embodiments, the concentration of the reporter binding moiety is about 1000 times greater than the concentration of the reporter.

In some embodiments, the concentration of the reporter is in a picomolar range. For example, the concentration of the reporter may be less than about 300 pM. In some embodiments, the concentration of the reporter is from about 10 pM to about 140 pM, or from about 40 pM to about 140 pM, from about 40 pM to about 100 pM, or from about 60 pM to about 100 pM, or from about 80 pM to about 100 pM, or from about 100 pM to about 140 pM. In some embodiments, the concentration of the reporter is about 20 pM, or about 40 pM, or about 60 pM, or about 80 pM, or about 100 pM. In some embodiments, the concentration of the reporter is about 120 pM.

In some embodiments, the concentration of the reporter binding moiety is in a nanomolar range. For example, the concentration of the reporter binding moiety may be greater than about 1 nm. In some embodiments, the concentration of the reporter binding moiety is from about 1 nm to about 60 nM, or from about 1 nm to about 50 nM, or from about 1 nm to about 40 nM, or from about 1 nm to about 30 nM, or from about 1 nm to about 20 nM, or from about 1 nm to about 15 nM, or from about 1 nm to about 10 nM, or from about 1 nm to about 5 nM. In some embodiments, the concentration of the reporter binding moiety is from about 100 nm to about 700 nM, e.g., about 100 nM, or about 200 nM, or about 300 nM, or about 400 nM, or about 500 nM, or about 600 nM, or about 600 nM.

In some embodiments, the concentration of the reporter binding moiety ranges from about 1 nM to about 10 nM, and the concentration of the reporter ranges from about 15 pM to about 25 pM. In some embodiments, the concentration of the reporter binding moiety is about 5 nM and the concentration of the reporter is about 20 pM.

Various tags and corresponding tag binding partners can be used in accordance with embodiments of the present disclosure. In some embodiments, the tag comprises biotin and the tag binding partner comprises avidin (e.g. streptavidin). In some embodiments, the tag comprises biotin and the tag binding partner comprises streptavidin. In some embodiments, the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag and the tag binding partner comprises an anti-Etag antibody (GAPVPYPDPLEPR (SEQ ID NO: 1)), or the tag comprises FLAG and the tag binding partner comprises an anti-FLAG antibody (DYKDDDDK (SEQ ID NO: 2), or the tag comprises Myc and the tag binding partner comprises an anti-Myc antibody (EQKLISEEDL (SEQ ID NO: 3), or the tag comprises HA and the tag binding partner comprises an anti-HA antibody (YPYDVPDYA (SEQ ID NO: 4), or the tag comprises SNAP and the tag binding partner comprises a benzylguanine derivative, or the tag comprises "CLIP", and the tag binding partner comprises a benzylcytosine derivative.

Various tags can be used in methods and kits in accordance with embodiments of the present disclosure. The tags can be various peptide tags, covalent peptide tags, protein tags, and other suitable types of tags.

Various reporters can be used in embodiments of the present disclosure. In some embodiments, the reporter molecule is a metal core and a silica shell or the reporter; wherein the silica shell is optionally impregnated with a plurality of quantum dots; and wherein the metal core optionally comprises gold. In some embodiments, the reporter comprises a plurality of quantum dots, quantum-dot-studded particles, a single quantum dot, a single quantum-dot-studded particle, organic dye, upconverting phosphors, and other types.

In some embodiments, the reporter is a fluorescent reporter, a phosphorescent reporter, or a colorimetric reporter.

In some embodiments, the reporter may be a fluorescent reporter, a phosphorescent reporter, or colorimetric reporter such as a colored particle for measuring absorbance and/or scattering of light (or, for example, the presence absence of a certain color through colorimetric analysis). In some embodiments, any suitable detectable reporter as is known in the art can be used. For example, the detectable reporter can be a radioactive reporter (such as, e.g. 3H, 125I, 35S, 14C, 32P, and 33P), an enzymatic reporter (such as, e.g. horseradish peroxidase, alkaline phosphatase, glucose 6-phosphate dehydrogenase, and the like), a chemiluminescent reporter (such as, e.g., acridinium esters, thioesters, or sulfonamides; luminol, isoluminol, phenanthridinium esters, and the like), a fluorescent reporter (such as fluorescein (e.g., 5-fluorescein, 6-carboxyfluorescein, 3'6-carboxyfluorescein, 5 (6)-carboxyfluorescein, 6-hexachloro-fluorescein, 6-tetrachlorofluorescein, fluorescein isothiocyanate, and the like)), rhodamine, phycobiliproteins, R-phycoerythrin, quantum or metal containing (Mc) dots (e.g., zinc sulfide-capped cadmium selenide), a thermometric reporter, or an immunopolymerase chain reaction reporter. In various embodiments, the reporter can include, without limitation, fluorophores, chromophores, radioisotopes, magnetic particles, gold particles, enzyme substrates, and the like. In some embodiments, the reporter is a chemiluminescent or fluorescent protein, such as, for example, green fluorescent protein (GFP), enhanced green fluorescent protein (EGFP), *Renilla reniformis* green fluorescent protein, GFPmut2, GFPuv4, yellow fluorescent protein (YFP), enhanced yellow fluorescent protein (EYFP), cyan fluorescent protein (CFP), enhanced cyan fluorescent protein (ECFP), enhanced blue fluorescent protein (EBFP), citrine and red fluorescent protein from discosoma (dsRED), luciferase, umbelliferone, rhodamine, fluorescein, dichlorotriazinylamine fluorescein, dansyl chloride, phycoerythrin, and the like. In some embodiments, the reporter is a non-protein organic fluorophore of any of the following families: xanthene derivatives, such as fluorescein, rhodamine, Oregon green, eosin, and Texas red; cyanine derivatives, such as cyanine, indocarbocyanine, oxacarbocyanine, thiacarbocyanine, and merocyanine; squaraine derivatives and ring-substituted squaraines, including Seta, SeTau, and Square dyes; naphthalene derivatives (dansyl and prodan derivatives); coumarin derivatives; oxadiazole derivatives, such as pyridyloxazole, nitrobenzoxadiazole and benzoxadiazole; anthracene derivatives, such as anthraquinones, including DRAQ5, DRAQ7 and CyTRAK Orange; pyrene derivatives, such as cascade blue, etc.; oxazine derivatives, such as Nile red, Nile blue, cresyl violet, oxazine 170, etc.; acridine derivatives, such as proflavin, acridine orange, acridine yellow, etc.; arylmethine derivatives, such as auramine, crystal violet, malachite green; and tetrapyrrole derivatives, such as porphin, phthalocyanine, bilirubin. In various embodiments, the reporter includes without limitation enzymatic reporters, e.g., enzymes such as horseradish peroxidase, alkaline phosphatase, beta-galactosidase, glucose 6-phosphate dehydrogenase, and the like. In some embodiments, the reporter may be one or more quantum dots or quantum-dot-studded particles. In some embodiments, the reporter may include a metal core (i.e., gold core) with a silica shell, wherein the silica shell is impregnated with a plurality (e.g., 100-600) quantum dots (e.g. quantum-dot-studded particles). Any other number of quantum dots can be used.

In embodiments, the method employs a relatively low amount of quantum dots or quantum-dot-studded particles, e.g. about 400 pM or less, or about 300 pM or less, or about 200 pM or less, or about 100 pM or less, or about 50 pM or less, or about 10 pM or less, e.g. about 400 pM, or about 300 pM, or about 200 pM or less, or about 100 pM, or about 50 pM, or about 10 pM. Various analytes can be detected using the methods in accordance with embodiments of the present disclosure. In some embodiments, the analyte comprises one or more of human chorionic gonadotropin (hCG), luteinizing hormone (LH)/Lutropin, prostate specific antigen (PSA), herpes simplex virus (HSV) antibodies, estrone-3-glucuronide (E3G), bacteria, hemoglobin A1C, C-reactive protein (CRP), an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof. In some embodiments, the analyte additionally or alternatively comprises one or more of N-terminal (NT)-pro hormone BNP (NT-proBNP), C-reactive protein (CRP), D-Dimer, Vitamin-D, Vitamin B12, T3, T4, Thyroid-stimulating hormone (TSH), Parathyroid hormone (PTH), Follicle stimulating hormone (FSH), Ferritin, luteinizing hormone (LH), human chorionic gonadotropin (hCG), Progesterone, Estradiol, Testosterone, Prostate-specific antigen (PSA), and Homocysteine.

In some embodiments, an analyte can be or can comprise an antigen and/or a biomarker for a biological event. In some embodiments, the biological events may include a disease event (e.g., disease biomarker), an inflammation event (e.g., an inflammation biomarker), a reproduction event (e.g., a reproduction biomarker), and/or an aging event (e.g., an aging biomarker). Disease biomarkers may include one or more disease biomarkers related to or associated with the onset of disease, the offset of disease, and/or the presence of a disease state in a patient. Disease biomarkers may include one or more of a viral biomarker, a bacterial biomarker, a cancer biomarker, or a symptom biomarker. Viral biomarkers may include, but are not limited to biomarkers for common cold (e.g. rhinovirus), influenza, herpes, Zika, and/or HIV. In some embodiments, viral biomarkers may include herpes simplex virus (HSV), one or more rhinovirus proteins, one or more influenza A/B/C proteins, one or more HSF-1/2 proteins, and/or one or more HIV virus proteins. Bacterial biomarkers may include, but are not limited to, biomarkers for strep throat (i.e., Streptococcus-A (Strep-A)), biomarkers for Chlamydia, and/or biomarkers for gonorrhea. In some embodiments, bacterial biomarkers may include, but are not limited to, one or more streptococcus proteins, one or more Chlamydia trachomatis proteins, and/or one or more Neisseria gonorrhoeae proteins. Symptom biomarkers may include, but are not limited to, biomarkers for coughing, wheezing, runny nose, nausea, cramps, tightness of the chest, light-headedness, sore throat, and/or chest pain. Disease biomarkers may also include, but are not limited to, biomarkers for cardiac distress and/or diabetes. In some embodiments, disease biomarkers may include troponin, CRP, and/or ha1c. Cancer biomarkers may include biomarkers for prostate cancer, breast cancer, colorectal cancer, gastric cancer, GIST, leukemia/lymphoma, lung cancer, melanoma, and or pancreatic cancer. In some embodiments, prostate cancer biomarkers may include PSA. In some embodiments, breast cancer biomarkers may include one or more of ER/PR and HER-2/neu. In some embodiments, colorectal cancer biomarkers may include one or more of EGFR, KRAS, and UGT1A1. In some embodiments, gastric cancer biomarkers may include HER-2/neu. In some embodiments GIST biomarkers may include c-KIT. In some embodiments, leukemia/lymphoma biomarkers may include one or more of CD20 antigen, CD30, FIP1L1-PDGRFalpha, PDGFR, PML/RAR alpha, TPMT, and UGT1A1. In some embodiments, lung cancer biomarkers may include one or more of ALK, EGFR, and KRAS. In some embodiments, melanoma biomarkers may include BRAF. Inflammatory biomarkers, which may include anti-inflammatory biomarkers, may include one or more inflammatory biomarkers described in U.S. Patent Application Publication No. 2010/0275282, the entirety of which is incorporated herein by reference. Reproduction biomarkers may include biomarkers for ovulation, fertilization, implantation, and/or embryo development. In some embodiments, reproduction biomarkers may include β-human Chorionic Gonadotropin (β-hCG or hCG), hyperglycosylated hCG, luteinizing hormone (LH), estrone-3-glucuronide (E3G), early pregnancy factor (EPF), and/or pre implantation factor. Aging biomarkers or age-related biomarkers include one or more biomarkers described in U.S. Patent Application Publication No. 2008/0124752, the entirety of which is incorporated herein by reference. Other antigens/biomarkers of interest include, but are not limited to, any antigens/biomarkers associated with SARS-COV-2, MERS, SARS, Hand foot and mouth disease, cardiac biomarkers, thyroid hormone, obesity biomarkers, biomarkers relating to bleeding disorders such as vWF, Factor 8, Factor 10, fifths disease, cold, flu, Ebola, E coli, Listeria, and Salmonella.

In embodiments, the sample is or comprises whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, pus, and combinations thereof. In some embodiments, the sample is whole blood, plasma, serum, or urine. In addition, the sample can be of any other nature, as embodiments are not limited to any specific type of a sample in which analyte(s) can be detected.

The methods in accordance with embodiments of the present disclosure allow detection of various analytes in a sample. In some embodiments, an analyte of interest comprises an antigen. In some embodiments, a capture moiety of a magnetic conjugate comprises an antibody configured to bind an analyte. Non-limiting examples of antigens include infectious disease antigens, such as, e.g., coronavirus antigens, influenza antigens (e.g. surface proteins hemagglutinin (H and neuraminidase (NA)), etc.

In some embodiments, an analyte of interest comprises an antibody. In embodiments, non-limiting examples of antibodies being detected include one or more of IgG, IgM, IgD, IgA, and IgE antibodies.

In embodiments, the antibody being detected is an antibody directed against a pathogen antigen, e.g., without limitation, a coronavirus antigen. The coronavirus antigen can be, e.g., an IgG antibody. In some embodiments, antibodies of interest comprise IgG and/or IgM antibodies. The coronavirus is a member of the Coronaviridae family, optionally selected from (a) a betacoronavirus, optionally selected from severe acute respiratory syndrome coronavirus 2 (SARS-COV-2), severe acute respiratory syndrome coronavirus (SARS-COV), middle east respiratory syndrome coronavirus (MERS-COV), HCoV-HKU1, and HCoV-OC43, and (b) an alphacoronavirus, optionally selected from HCoV-NL63 and HCoV-229E. In embodiments, the coronavirus is SARS-COV-2.

In some embodiments, a capture moiety of the magnetic conjugate comprises a first antibody configured to bind the analyte, wherein a reporter binding moiety comprises a second antibody configured to bind the analyte. In such embodiments, the analyte can comprise an antibody, and a capture moiety of the magnetic conjugate can comprise an antigen configured to bind the antibody. The method may indicate whether the subject is producing or not producing antibodies directed against an antigen. In some embodiments, the method may provide an amount of antibodies in the sample.

In some embodiments, the capture moieties and the reporter binding moiety bind different portions of the analyte. In some embodiments, the capture moieties and the reporter binding moieties are different. In some embodiments, the capture moieties and the reporter binding moieties bind to different antigens or epitopes.

In embodiments of the present disclosure, use of a reporter binding moiety that has a tag bound thereto and that is configured to associate with a reporter via a tag binding partner that can interact with a tag (e.g. via an antigen-antibody interaction), allows substantially increasing the speed of the detection. A concentration of the reporter binding moiety can be substantially greater than a concentration of the reporter—e.g., the concentration of the reporter binding moiety can be in a nanomolar range, whereas the concentration of the reporter can be in a picomolar range. In some embodiments, a concentration of the reporter binding moiety can be about $10^{-6}$ M, or about $10^{-7}$ M, or about $10^{-8}$ M. In some embodiments, a concentration of the reporter binding moiety can be at least about $10^{-6}$ M, or at least about $10^{-7}$ M, or at least about $10^{-8}$ M. The concentration of the reporter can be less than about $10^{-11}$ M, or no greater than $10^{-11}$ M. Thus, the kinetics of the creation of a detectable complex (i.e. the complex comprising the analyte bound to a magnetic particle and to a reporter) is dramatically improved, in some cases by 1000 times faster.

Also, the proportion of bound, detectable analytes, as compared to the entire amount of the analyte in a sample (including detectable and undetected analytes present in the sample), can be improved significantly, up to 100% in some case. In some embodiments, the proportion of bound, detectable analytes is at least 80%, or at least 85%, or at least 90%, or at least 95%, or at least 98%, or at least 99%, or about 100%.

In embodiments, a signal-to-noise ratio is increased, background noise is reduced, and specificity and sensitivity are increased.

In some embodiments, the sample has a volume of about 1 microliter. In some embodiments, the sample has a volume of smaller than 1 microliter. In some embodiments, the sample has a volume of about 2 microliters, or about 3 microliters, or about 4 microliters, or about 5 microliters.

In some embodiments, e.g. in which the detected analytes comprise antibodies, the method further comprises a step of pre-treating the sample with a magnetic conjugate comprising a magnetic particle and a moiety configured to bind contaminant antibodies and/or non-antibody moieties. In some embodiments, the contaminant antibodies are not directed against the antigen configured to bind the antibody or are ineffective at generating an immune response against the antigen configured to bind the antibody. In some embodiments, wherein the pre-treating reduces or eliminates one or more of: (a) heterophile antibodies; (b) antibodies that non-specifically interact with the magnetic particle; and (c) non-antibody moieties that non-specifically interact with the magnetic particle.

In some embodiments, the method is suitable for point-of-care usage. In some embodiments, the method is suitable for field usage and/or the method is suitable for home usage.

In some embodiments, the methods are compatible with the World Health Organization's ASSURED (affordable, sensitive, specific, user-friendly, rapid and robust, equipment-free, and deliverable) criteria.

In some embodiments, the method is substantially free of false positives. In some embodiments, the method is substantially free of false negatives.

In some embodiments, the method provides better (i.e. greater) sensitivity and specificity than a solid phase immunoassay method, a bead-based flow cytometry, or a lateral flow immunochromatographic assay.

In some embodiments, the method provides better sensitivity and specificity than a method using a bead-based flow cytometry-based assays, optionally bead-based, flow cytometry-based assays. In some embodiments, the method provides better sensitivity and specificity than a method using a lateral flow immunochromatographic assay.

In some embodiments, the method provides an increased signal-to-noise ratio as compared to a method using a solid phase immunoassay.

In some embodiments, the method provides reduced background noise as compared to a method using an assay in which a concentration of the reporter binding moiety is not substantially different from a concentration of the reporter.

In some embodiments, the method provides an increased signal-to-noise ratio as compared to a method using an assay in which a concentration of the reporter binding moiety is not substantially different from a concentration of the reporter.

In some embodiments, the method provides better sensitivity and specificity than a method using an assay in which a concentration of the reporter binding moiety is not substantially different from a concentration of the reporter.

In various aspects, the present invention provides a kit suitable for the method of any of the embodiments disclosed herein. The kit may comprise a magnetic conjugate, a reporter binding moiety, and a reporter. The kit can be configured such that a concentration of the reporter binding moiety is substantially greater than a concentration of the reporter.

In embodiments, the methods in accordance with the present disclosure employ a nanoparticle-based immunoassay configured to detect the presence, absence, or level of the antibody by detecting the reporter. In some embodiments, the immunoassay can be implemented similar to assays described in PCT/US2018/015440 (published as WO2018140719), or as a variation or combination of those assays, the disclosure of which is incorporated by reference herein in its entirety.

Immunoassays

Methods described herein include methods for detecting the presence, absence, or amount of an analyte in a biological sample.

In certain embodiments, the methods described herein encompass a sandwich method, a separate addition method, a competitive assay method, a tertiary (three binding event) method, a whole cell assay method, or any combinations thereof.

For example, the sandwich method may be well suited for processing small fluid sample volumes. The separate addition method described herein may enable processing of larger fluid volumes, with improved sensitivity. The competitive assay method may be useful, e.g., for assaying analytes in scenarios in which a matched pair of a capture moiety and a corresponding reporter binding moiety that would bind to an analyte simultaneously is not available. The tertiary assay method may encompass three binding events to enhance the kinetics of a system employed for the present method.

FIGS. 1A-1E illustrate schematically components that are involved in an assay in accordance with embodiments of the present disclosure. The assay shown in FIGS. 1A-1E is a sandwich assay, and an analyte of interest is shown by way of example only as HCG. It should however be appreciated that any other analyte of interest can be detected using the described methods.

Left panel of FIG. 1A illustrates an analyte of interest (HCG, shown only by way of example, in green), a capture moiety shown as an antibody #1 (in blue) that is specific to the analyte of interest, and a reporter binding moiety shown as antibody #2 (in orange) that is also specific to the analyte of interest. FIG. 1A (left panel) also shows that the antibodies #1&2 are able to simultaneously bind to the analyte of interest. The assay also includes a reporter ("colored reporter," shown as a yellow sun symbol), a magnetic particle, and a tag shown by way of example only as biotin. Although not shown in FIGS. 1A-1E, the reporter has a tag binding partner bound thereto and configured to bind the tag bound to the reporter binding moiety.

FIG. 1A further shows, in right panel, magnetic particles bound to the antibody #1, biotin bound to the antibody #2, and the analyte.

FIG. 1B further illustrates (in right panel, the left panel is identical to the left panel of FIG. 1A) that the antibodies #1 and #2 can simultaneously bind the analyte, thereby forming a complex comprising the magnetic particle with the antibody #1 bound thereto and the reporter binding moiety with a tag (biotin, in which example) bound thereto. The formation of the complex shown in FIG. 1B (right panel) can occur in one step (when both the magnetic particle and reporter binding moiety are added to a reaction mixture) or in two steps (when the magnetic particle and reporter binding moiety are separately added to a reaction mixture).

After the complex as shown in FIG. 1B is formed, a magnetic pull down can be performed to separate the analyte from the rest of the sample. The excess reporter binding moiety can be removed, and the sample (including the analyte) can be resuspended with a relatively low concentration of reporter, as shown schematically in FIG. 1C. A concentration of the reporter binding moiety is substantially greater than a concentration of the reporter. It should be appreciated that, even though the present disclosure refers to "the sample" throughout the assay, the sample may not be in the original form as obtained from a subject or from another source. The sample will be in the reaction mixture that includes other ingredients and the mixture he sample can be subjected to sonication, removal of a portion of the mixture, resuspension, and other manipulations. The reaction mixture, including at least a portion of the sample, may or may not include an analyte of interest.

As shown in FIG. 1D, each reporter becomes associated with a reporter binding moiety. The reporter may have a tag binding partner (e.g., streptavidin). At the time the reporter is added to the reaction mixture, the final complex (can be referred to as a "sandwich," in this example) is a limiting reagent, and the reporter is in large excess relative to the sandwich complexes, although the reporter's concentration is orders of magnitude lower than that of a reporter binding moiety.

FIG. 1E illustrates that, when a magnetic field is applied to separate the analyte (in the final, detectable complex with the magnetic conjugate, reporter binding moiety, and reporter) from the sample, excess of the reporter (i.e. unbound reporter particles) is removed (washed away).

In the illustrated example, during the final complex formation, an analyte is a limiting reagent and the higher concentrations of the other binding moieties allow the fraction of the analyte that is bound, as well as maximizing the speed at which this binding happens.

In embodiments, a reporter binding moiety is bound to a tag and a reporter is bound to a tag binding partner, and the tag and the tag binding partner are configured to interact. A concentration of the reporter binding moiety is substantially greater than a concentration of the reporter.

In a conventional immunoassay assay, a magnetic particle with a capture moiety (e.g., antigen) binds an analyte (e.g., an antibody) that is also bound to a reporter binding moiety of a reporter conjugate that is formed from a reporter and a reporter binding moiety. In this way, a complex (e.g., a "sandwich") is formed. The kinetics of formation of the complex in a traditional assay (e.g. ELISA) is described below.

A magnetic particle with a capture moiety (e.g., antibody) bound thereto (i.e. a magnetic conjugate) can bind to an analyte (e.g. an antigen) in a sample first, or a reporter conjugate ("RC") can first bind to the analyte. In the illustration below, it is assumed that the magnetic conjugate binds to the analyte first, forming a complex ("C1") of the magnetic conjugate with the analyte bound thereto. The reporter conjugate ("RC") can then bind to the complex C1. It should be appreciated however that the reporter conjugate can alternatively bind to the analyte before the magnetic conjugate binds to the analyte.

As shown in Equation (1) below, in a typically immunoassay, the rate of formation of a final complex $$\left(\frac{d[\text{Complex}]}{dt}\right)$$

is defined as a concentration of the magnetic conjugate with the analyte bound thereto ([C1]), multiplied by a concentration of the reporter conjugate ("RC") and multiplied by an association rate constant of a reporter binding moiety ($K_{ON_R}$). The [C1] concentration of the magnetic conjugate with the analyte bound is proportional to the concentration of the analyte in the sample, and this is the value that is being measured in the assay. The [RC] concentration of the reporter is typically $10^{-11}$ M, though other values can be used (e.g., $10^{-9}$ M or $10^{-10}$ M). The concentration of the reporter conjugate is limited by various factors, e.g. colloidal stability of reporter particles. The $K_{ON_R}$ is typically $10^5$ M.

The reporter conjugate may fall off the analyte with a certain off-rate (a dissociation rate constant of a reporter binding moiety ($K_{OFF_R}$), such that formed complexes will be lost at a concentration of [Complex] $K_{OFF_R}$. Typically, $1/K_{OFF_R}$ is 1.5-6 hours. In a typical immunoassay (e.g. ELISA), there are long incubation steps and long wash steps, and $K_{OFF_R}$ becomes meaningful. Equation (2) below illustrates an equilibrium state (i.e. when no change in the complex formation occurs). The dissociation constant of the reporter binding moiety, $K_D$, can then be expressed as shown by Equation (3). The right part of Equation (3) is an equilibrium ratio that is dictated by $K_{OFF_R}$, $K_{ON_R}$, or by $K_D$ of the reporter binding moiety (e.g. antibody). This defines a fraction of an analyte that is in a detectable form versus a fraction of an analyte in an undetectable form.

$$\frac{d[\text{Complex}]}{dt} = [C1][RC]K_{ON_R} - [\text{Complex}]K_{OFF_R} \quad (1)$$

-continued $$\text{Equilibrium} = \frac{d[\text{Complex}]}{dt} = 0 \qquad (2)$$

$$K_D = \frac{K_{OFF}}{K_{ON}} = \frac{[C1][RC]}{[\text{Complex}]} \qquad (3)$$

Equations (1) through (3) above illustrate generally limitations of a typical immunoassay, including long incubation times that are driven by a slow nature of the reporter binding moiety kinetics and are limited by ability to increase a concentration of the reporter binding moiety without decreasing quality of the signal (i.e. getting nonspecific signal).

To overcome limitations of the present disclosure, in methods in accordance with the embodiments of the present disclosure, the step of binding the reporter conjugate to the analyte of interest is replaced with a step of binding a reporter binding moiety with a tag bound thereto and a step of binding a reporter with a tag binding partner bound thereto. FIG. 2 illustrates schematically components of an immunoassay in accordance with some embodiments of the present disclosure, as well as intermediate complexes and a final complex that are formed as part of the immunoassay. In this example, an analyte 100 comprises an antigen (which is shown by way of example only). Both a capture moiety of a magnetic conjugate 102 and a reporter binding moiety 103 (with a tag bound thereto) are antibodies, which can be the same or different antibodies.

As shown in FIG. 2, and as also illustrated in Equation (4) below, in the example illustrated, the first step of the assay may be the same as in the conventional assay-binding of a magnetic conjugate 102 with an analyte 100 bound thereto to form a complex C1 (104), with the concentration expressed as [C1]. The use of the reporter binding moiety with a tag bound thereto allows having the reporter binding moiety at a greater concentration than a concentration of the reporter (103 in FIG. 2). FIG. 2 further shows a reporter 105 with a tag binding partner bound thereto. FIG. 2 also illustrates complexes that can be formed in the reaction mixture, such as a complex 107 comprising the analyte and the reporter binding moiety with the tag, and a complex 109 comprising the reporter binding moiety and the reporter associated via the tag-tag binding partner interaction (without the analyte).

As shown in Equation (4) below and in FIG. 2, the rate of formation of the final complex (120 in FIG. 2) depends on a concentration of a complex 106 ([C3]) comprising the magnetic conjugate 102 and the reporter binding moiety 103 bound to the analyte 100. The formation of the complex 106 is expressed as shown in Equation (5) where [TAB] denotes a concentration of the tagged reporter binding moiety 103 (i.e., in this example, a "tagged antibody"). The concentration of C3 ([C3], in the reaction is proportional to the amount of the analyte (i.e. antigen, in this example).

In Equation (4), instead of the $K_{ON_R}$ and $K_{OFF_R}$ terms, terms $K_{ON_L}$ and $K_{OFF_L}$ are used which are association and disassociation rate constants of a "linker"—i.e. the interaction between the tag of the reporter binding moiety 103 and the tag binding partner of the reporter 105.

$$\frac{d[\text{Complex}]}{dt} = [C3][RC]K_{ON_L} - [\text{Complex}]K_{OFF_L} \qquad (4)$$

-continued $$\frac{d[C3]}{dt} = [C1][\text{TAB}]K_{ON_R} - [C3]K_{OFF_R} \qquad (5)$$

With reference to Equation (5), like in the traditional assay (see Equation (1)), $K_{ON_R}$ can be about $10^5$ M. However, in Equation (4), while [RC] is about $10^{-11}$ M, for the linker, $K_{ON_L}$ can be about $10^8$ M. Accordingly, the formation of the complex in accordance with Equation (4) is a thousand times faster than the formation of the complex in accordance with Equation (1) showing the kinetics of the conventional assay.

Thus, even though, in the illustrated method in accordance with embodiments of the present disclosure, the concentration of the reporter can be about the same as in the conventional assay, the rate of formation of the complex is dramatically faster than in the conventional assay. Furthermore, the concentration of the tagged reporter binding moiety 103 (FIG. 2) (shown as [TAB] in Equation (5) can be increased as compared to the conventional assay, e.g. it can be about $10^{-6}$ M. In some embodiments, the concentration of the tagged reporter binding moiety can be about $10^{-7}$ M or $10^{-8}$ M. Thus, in a method in accordance with embodiments of the present disclosure, the concentration of the tagged reporter binding moiety is much higher than the [RC] concentration of the reporter (e.g. about $10^{-11}$ M) in the conventional assay. Also, even though, instead of using a reporter conjugate as in a conventional assay, the present methods make use of separate binding events (of a reporter binding moiety method having a tag bound thereto and of a reporter having a tag binding partner bound thereto), these two separate steps are an order of magnitude, or more, faster than the step of binding a reporter conjugate in a conventional assay. This boosted kinetic allows performing the entire assay in a range from about 1 minute to about 20 minutes. Also, the term [Complex] $K_{OFF_L}$ in Equation (4) and the term [C3] $K_{OFF_R}$ in Equation (5) become negligible (approximately zero). The assay can have about 100% bound rate such that, with reference to FIG. 2, most or all of the analyte 100 is in the bound form in the final detectable complex 120.

In some embodiments, the concentration of a reporter binding moiety is about from hundreds picomolar to hundreds nanomolar. In some embodiments, the concentration of a reporter is from about 1 pM to about 600 pM, e.g., in some embodiments, from about 40 pM to about 120 pM.

In embodiments, a concentration of magnetic particles used in an immunoassay can be about the same as an expected concentration of analyte molecules in a sample. In some embodiments, a concentration of magnetic particles used in an immunoassay can be greater than an expected concentration of analyte molecules in a sample. Also, in embodiments in which a magnetic particle has more than one capture moiety bound thereto (e.g., 3-4 capture moieties, or any other number of capture moieties such as, e.g., antibodies), a number of the binding sites on the magnetic particle can be higher than an expected concentration of analyte molecules in a sample.

In some embodiments, more than one analyte can be detected. This can be done in parallel, e.g., in separate reactions (e.g., without limitations, separate wells of a well plate).

In some embodiments, methods in accordance with the present disclosure can be used to detect the presence, absence, or amount of a plurality of analytes in a biological sample simultaneously, in the same sample. By tagging each analyte with a reporter particle having a certain property (e.g., capable of generating a signal of a specific color), the described approach can be used for simultaneous detection of multiple analytes in the same sample.

In some embodiments, such multiplexing method comprises (a) contacting the sample with at least one magnetic conjugate comprising a magnetic particle and a plurality of capture moieties coupled to the magnetic particle and each configured to bind a corresponding analyte of the plurality of analytes; (b) contacting the magnetic conjugate with a plurality of reporter binding moieties each having a corresponding tag bound thereto, each reporter binding moiety being configured to bind a corresponding analyte of the plurality of analytes; (c) contacting the magnetic conjugate with a plurality of reporters each having a corresponding tag binding partner bound thereto that is configured to bind a corresponding tag thereby optionally associating a reporter binding moiety bound to the tag with a corresponding reporter, wherein each reporter is configured to generate a corresponding different signal; (d) applying a magnetic field to separate the magnetic conjugate, optionally having an analyte of the plurality of analytes that has the corresponding reporter binding moiety associated with the corresponding reporter bound thereto and (e) detecting the presence, absence, or level of each analyte of the plurality of analytes based on detection of a signal generated by each of the reporters.

In multiplexing embodiments in which more than one analyte can be detected in the same sample, tag-tag binding partner pairs may be orthogonal, such that a tag binds only a corresponding tag binding partner, and vice versa. Thus, for detection of certain analytes in a sample, tag-tag binding partner pairs can be selected such that no interaction can occur between tag and tag binding partners from different pairs. In other words, each tag-tag binding partner pair is selected to be specific to a particular analyte of the plurality of analytes to be detected.

In multiplexing embodiments, the reporters, each bound to a respective analyte (if the analyte is present in the sample), generate corresponding signals of different properties, such as colors, and the method thus allows to discriminate between different analytes in the sample.

In embodiments, the methods described herein employ nanoparticle-based immunoassays configured to perform the present detection of the presence, absence, or amount of an analyte in a biological sample. The nanoparticle-based immunoassays can be implemented as part of a testing platform which can be a portable system in some implementations. The system can be in the form of a kit including all the components necessary to perform the present detection.

In some embodiments of the method implemented in accordance with a sandwich immunoassay method, a reporter can be, e.g., one or more gold core particles with a silica shell impregnated with 100-600 quantum dots (e.g. from nanoComposix, San Diego, CA). In some embodiments, the reporter comprises one or more quantum dots or quantum-dot-studded particles, or another nanoparticle.

In some embodiments, a reporter can be used that is a bright reporter (i.e. generates a signal of high quality), has high surface area, and remains colloidally stable during the analysis. For example, in some embodiments, such reporter can be a particle that includes a large number (e.g., several hundred) of highly fluorescent quantum dots or quantum-dot-studded particles providing up to about 300× optical amplification of the signal.

The sandwich immunoassay involves detection of whether a complex is formed that comprises a magnetic conjugate, an analyte of interest, and a reporter binding moiety associated with a corresponding reporter that is bound thereto via a tag-tag binding partner interaction. In embodiments, the magnetic conjugate comprises a magnetic particle and a capture moiety coupled to the magnetic particle and configured to bind an analyte of interest in the sample.

The complex ("sandwich") is formed only in the presence of the analyte. When the analyte is present, the resulting complex can be attracted by a magnet and provides an optical signal that increases its intensity as the analyte concentration increases.

The sandwich complex cannot form in absence of the analyte, because the reporter binding moiety/reporter system does not bind with the magnetic conjugate. When not associated with a magnetic particle, the reporter is washed away and does not generate a signal when the sample is analyzed.

In some embodiments of the sandwich immunoassay method, a magnetic conjugate (comprising a magnetic particle and a capture moiety coupled to the magnetic particle and configured to bind an analyte), a reporter binding moiety (having a corresponding tag bound thereto, the reporter binding moiety being configured to bind the analyte), and a reporter (having a corresponding tag binding partner bound thereto such that the tag binding partner can bind a corresponding tag thereby associating a reporter binding moiety bound to the tag with a corresponding reporter) may be added to an analysis chamber and mixed with a biological sample which may including an analyte of interest. A magnetic field may be applied (a "pulldown") by a magnet to separate the analyte from the sample. The pulldown can be performed by applying a magnetic field to the sample (with other ingredients added) for a certain time period (e.g., about 1 minute, or about 2 minutes, or about 3 minutes, or about 4 minutes, or about 5 minutes, or about 6 minutes, or about 7 minutes). In some embodiments, the magnetic field is applied for about 5 minutes. It should be appreciated however that the magnetic field can be applied to the sample for any suitable duration of time.

If the reporter is a fluorescence signal reporter (e.g., an organic dye, nanomaterial, or conjugated polymer), light may then be transmitted through at least a portion of the analysis chamber to cause the reporter to fluoresce. Such fluorescence may be detected by a suitable detector. In the absence of the analyte of interest, the reporter is not pulled down with the analyte and no fluorescence occurs.

In some embodiments, the method described herein may comprise: (a) contacting a sample with a magnetic conjugate comprising a magnetic particle and a capture moiety coupled to the magnetic particle and configured to bind an analyte in the sample; (b) contacting the magnetic conjugate with a reporter binding moiety having a tag bound thereto, the reporter binding moiety being configured to bind the analyte; (c) contacting the magnetic conjugate with a reporter having a tag binding partner bound thereto that is configured to bind the tag thereby optionally associating the reporter binding moiety bound to the tag with the reporter, wherein a concentration of the reporter binding moiety is substantially greater than a concentration of the reporter; (d) applying a magnetic field to separate the magnetic conjugate, optionally having associated therewith the analyte and the reporter binding moiety associated with the reporter bound thereto; and (e) detecting the presence, absence, or level of the analyte based on detection of a signal generated by the reporter.

In the above embodiment, a magnetic conjugate comprises a magnetic particle having a capture moiety coupled to the magnetic particle and configured to bind an analyte in a sample. In some embodiments, a magnetic conjugate comprises a magnetic particle having more than one capture moiety coupled thereto, such that more than one analyte (e.g., antigen) can be bound to the same magnetic particle.

If the reporter is a fluorescence signal reporter, light may then be transmitted through at least a portion of an analysis chamber carrying the sample to cause the reporter to fluoresce, and the emitted fluorescence is measured by a suitable detector. A signal generated by the reporter can be detected using, e.g., a light source and a photodetector.

In embodiments, a magnetic conjugate (comprising a magnetic particle and a capture moiety coupled to the magnetic particle), a reporter binding moiety, and a reporter can be added to the analysis chamber simultaneously or at different times. Thus, in some embodiments, a magnetic conjugate, a reporter binding moiety, and a reporter may be added separately. Furthermore, in some embodiments, a reporter binding moiety and a reporter can be pre-bound to each other.

In some embodiments, an immunoassay method is a separate addition method, which can be used for processing larger volumes of samples (though small samples can be analyzed as well) and which allows concentrating an analyte of interest. This approach may allow detecting an analyte in a sample with improved sensitivity. In the separate addition method, a magnetic conjugate may be added to an analysis chamber and mixed with a sample which may or may not include an analyte of interest. A pulldown may be performed by activating a magnetic field (such that an analyte, if present, binds with a capture moiety of the magnetic conjugate), and a volume (e.g. a portion) of the sample may be removed. An additional volume of the sample may then be added. After (or, in some cases, before) the additional volume of the sample is added, the magnetic field may be deactivated and the magnetic conjugate may again be mixed with the sample. This process may be repeated a certain number of times (e.g., one, two, three, four, or more than four times) to concentrate the analyte. After concentrating the analyte, the reporter binding moiety and the reporter may be added and mixed with the sample such that the reporter binding moiety binds the analyte and a tag bound to the reporter binding moiety is bound to a tag binding partner that is bound to a reporter, thereby the reporter binding moiety is associated with the reporter. A further magnetic pulldown may then be performed to separate the analyte from the sample, which (if present) is bound to the magnetic particle and the reporter (via the reporter binding moiety). If the reporter is a fluorescence signal reporter, light may then be transmitted through at least a portion of the analysis chamber to cause the reporter to fluoresce, and the emitted fluorescence is measured by a suitable detector. In the absence of analyte, the reporter will not be pulled down with the analyte and no fluorescence is detected.

In some embodiments, a competitive immunoassay method is performed, which can include two types of methods.

The method of a first type of the competitive immunoassay method can be used in scenarios in which an analyte (e.g., without limitation, an antigen, antibody, cell, bacteria, virus, etc.) is too small for simultaneously binding with a corresponding capture moiety (coupled to a magnetic particle, as part of a magnetic conjugate) and a reporter binding moiety (which may or may not be coupled to a reporter, e.g., via a tag-tag binding partner interaction). This method may also be used where either of the capture moiety and the reporter binding moiety is not available. In this method, a magnetic conjugate may be added to an assay chamber and mixed with a biological sample that may or may not include an analyte of interest. A reporter-labeled second analyte (which is an analyte, different form the analyte off interest) configured to bind the magnetic conjugate in the absence of the analyte of interest) may then be added and mixed with the sample. When the analyte of interest is present in the sample, the reporter-labeled second analyte does not bind to the magnetic conjugate because a binding site of a capture moiety of the magnetic conjugate is occupied by the analyte of interest. However, if the analyte of interest is not present in the analyzed sample, the magnetic conjugate will bind to the reporter-labeled second analyte. A magnetic pulldown is performed to separate the analyte of interest (if present) from the sample. If the reporter is a fluorescence signal reporter, light may then be transmitted through at least a portion of the analysis chamber to cause the reporter to fluoresce, and the emitted fluorescence is measured by a suitable detector. In the absence of the analyte of interest, the reporter-labeled analyte will be pulled down with the magnetic conjugate and no fluorescence is detected.

Accordingly, in some embodiments (e.g., in which a first type of the competitive immunoassay method is implemented), the method described herein may include the steps of: (a) contacting a sample with a magnetic conjugate comprising a magnetic particle and a capture moiety configured to bind an analyte of interest the sample; (b) contacting the sample with a reporter-labeled second analyte configured to bind the magnetic conjugate in the absence of the analyte in the sample; (d) applying a magnetic field to the analysis chamber to pull down the magnetic conjugate, optionally with the analyte associated therewith; and (e) detecting the presence, absence, or level of the analyte by detecting the reporter with a light source and photodetector. In the method, a concentration of the reporter binding moiety can be substantially greater than a concentration of the reporter.

In a second type of the competitive immunoassay method, a magnetic particle (e.g., a magnetic bead) may be used with a second, competitive analyte bound thereto (e.g., an antigen, antibody, or another type). The second analyte can be different from an analyte of interest. The second analyte can be, e.g., an antigen configured to bind a reporter binding moiety that is configured to bind the analyte of interest. In the absence of the analyte of interest, the second analyte (bound to the magnetic particle) binds the reporter binding moiety associated with a reporter. The resulting complex can be attracted by a magnet and provides an optical signal that decreases in intensity as a concentration of the analyte of interest in the sample increases. If the analyte of interest is present in the sample, it blocks complex formation. In particular, when the analyte of interest is present in the sample, it can preemptively bind the reporter binding moiety, competing for the formation of the complete complex with the second analyte bound to the magnetic particle. For example, when the analyte of interest is an antigen, it binds the available binding sites on the reporter binding moiety (i.e. an antibody) thus preventing the binding of the second analyte (bound to the magnetic particle) to the reporter binding moiety (bound to a reporter). In this way, the antibody binding sites on the reporter binding moiety are occupied by the analyte of interest and the analyte of interest is thus competing for the formation of the complete complex. Accordingly, when a magnetic field is applied, the second analyte, which is bound to the magnetic particle and not bound to the reporter, is pulled down. The analyte of interest that is bound to the reporter via the reporter binding moiety (the reporter and the reporter binding moiety may interact via a tag-tag binding partner interaction) is washed away. Therefore, an optical signal generated by the reporter decreases in intensity as concentration of the analyte of interest increases.

In the second type of the competitive immunoassay method, the magnetic particle can be coupled to the second analyte (to form what is referred to as a magnetic particle-labeled analyte) before the assay is performed. In some embodiments, the method involves the use of a reporter conjugate comprising a reporter and a reporter binding moiety. The reporter conjugate is added to an analysis chamber comprising a biological sample, and mixed with the sample which may include an analyte of interest. The magnetic particles with the second analyte bound thereto are added to the analysis chamber and mixed with the sample. A magnetic pulldown is then performed to separate the magnetic particles with the second analyte bound thereto from the sample. If the reporter is a fluorescence signal reporter, light may then be transmitted through the sample to cause the reporter to fluoresce, and the emitted fluorescence is measured by a suitable detector. In the presence of the analyte of interest, the magnetic particles having the second analyte bound thereto but not being associated with a reporter, are pulled down, resulting in the absence of fluorescence. Depending on the concentration of the analyte of interest in the sample, intensity of the signal generated by the reporter decreases as the analyte concentration increases.

Accordingly, in some embodiments (e.g., in which a second type of the competitive immunoassay method is implemented), the methods described herein may include the steps of: (a) contacting a sample with a reporter and a reporter binding moiety configured to bind an analyte of interest the sample; (b) contacting the sample with a magnetic particle-labeled second analyte configured to bind the reporter conjugate in the absence of the analyte of interest in the sample; (c) separating the magnetic particle-labeled analyte from the sample by applying a magnetic field to the sample; and (d) detecting the presence, absence, or level of the analyte by detecting the reporter. A concentration of the reporter binding moiety is substantially greater than a concentration of the reporter. The reporter can be detected, e.g., as described in the above embodiments, using a light source and photodetector.

As discussed above, in embodiments of the present disclosure, instead of using a reporter conjugate (i.e. a reporter binding moiety with a reporter bound thereto) as in a conventional immunoassay, a detection method can involve use of a reporter binding moiety having a tag bound thereto (instead of a reporter). The reporter binding moiety having a tag bound thereto and a reporter having a corresponding tag binding partner bound thereto can be added to a reaction mixture in two respective separate steps. The use of a reporter binding moiety with a tag bound thereto (and the use of the reporter with the corresponding tag binding partner) allows increasing a concentration of a reporter binding moiety, and a concentration of a reporter is substantially lower than the concentration of the reporter binding moiety. The speed of the final complex formation is increased dramatically, such that the entire assay can be performed in less than 20 minutes (e.g., in about 15 minutes), as compared to traditional assay that may take as long as 6 hours.

In some embodiments, the detection method comprises: (a) contacting a sample with a reporter binding moiety having a tag bound thereto and being configured to bind an analyte of interest in the sample; (b) contacting the sample with a reporter having a tag binding partner bound thereto such that the tag binding partner binds the tag thereby associating the reporter binding moiety bound to the tag with the reporter, wherein a concentration of the reporter binding moiety is substantially greater than a concentration of the reporter; (c) contacting the sample with a magnetic particle-labeled second analyte configured to bind the reporter binding moiety in the absence of the analyte of interest; (d) separating the magnetic particle-labeled second analyte from the sample by applying a magnetic field to the sample; and (e) detecting the presence, absence, or level of the analyte of interest based on detection of a signal generated by the reporter. The reporter can be detected, e.g., as described in the above embodiments, using a light source and photodetector.

In some embodiments, the tag comprises biotin and the tag binding partner comprises streptavidin, or the tag comprises fluorescein isothiocyanate (FITC) and the tag binding partner comprises anti-FITC antibody, or the tag comprises dinitrophenol (DNP) and the tag binding partner comprises anti-DNP antibody, or the tag comprises digoxigenin (DIG) and the tag binding partner comprises anti-DIG antibody, or the tag comprises Etag and the tag binding partner comprises an anti-Etag antibody (GAPVPYPDPLEPR (SEQ ID NO: 1), or the tag comprises FLAG and the tag binding partner comprises an anti-FLAG antibody (DYKDDDDK (SEQ ID NO: 2), or the tag comprises Myc and the tag binding partner comprises an anti-Myc antibody (EQKLISEEDL (SEQ ID NO: 3), or the tag comprises HA and the tag binding partner comprises an anti-HA antibody (YPYDVPDYA (SEQ ID NO: 4), or the tag comprises SNAP and the tag binding partner comprises a benzylguanine derivative, or the tag comprises "CLIP" and the tag binding partner comprises a benzylcytosine derivative.

In some embodiments, a method for detecting the presence, absence, or amount of an analyte in a biological sample may comprise: (a) contacting a sample with a reporter binding moiety, the reporter binding moiety having a tag bound thereto and being configured to bind an analyte in the sample; (b) contacting the sample with a reporter having a tag binding partner bound thereto such that the tag binding partner binds the tag thereby associating the reporter binding moiety bound to the tag with the reporter, wherein a concentration of the reporter binding moiety is substantially greater than a concentration of the reporter; (c) contacting the sample with a magnetic particle having a second analyte bound thereto, the second analyte being configured to bind the reporter binding moiety; (d) separating the magnetic particle having the second analyte bound thereto by applying a magnetic field to the sample; and (e) detecting the presence, absence, or level of the analyte by detecting the reporter. The reporter can be detected, e.g., as described in the above embodiments, using a light source and photodetector.

In some embodiments, a tertiary immunoassay method is implemented, which makes use of three binding events to enhance the kinetics of a system used in the present invention. The tertiary binding method can be applied to or can comprise the sandwich method, the separate addition method, and the competitive assay (first and second methods). The tertiary mode may involve the use of a reporter conjugate comprising a reporter having a tag binding partner bound thereto (e.g., fluorescent quantum dot functionalized with streptavidin) and a reporter binding moiety having a tag bound thereto (e.g., an antibody labeled with a biotin), and a magnetic conjugate comprising a magnetic particle and a capture moiety. The sample can be disposed in an analysis chamber.

The tertiary binding method may comprise adding the magnetic conjugate (comprising a magnetic particle and a capture moiety) to the analysis chamber and mixing the magnetic conjugate with the sample that may include an analyte of interest. A magnetic field may be applied (a "pulldown") to separate the analyte of interest from the sample. Volumes of sample may be removed and analyte concentration steps may be performed one or more times, as described above. The magnetic field may be deactivated and the reporter binding moiety (e.g., an antibody having a tag bound thereto) may be added to the analysis chamber, which may bind to the analyte of interest that is in turn bound to the magnetic conjugate. The reporter (having a tag binding partner bound thereto) may then be added to the analysis chamber, which may then bind to the reporter binding moiety, e.g., via a tag binding partner-tag interaction (e.g., a streptavidin-biotin binding interaction). A magnetic pull-down may then be performed to again separate the analyte of interest from the sample. If the reporter is a fluorescence signal reporter, light may then be transmitted through at least a portion of the analysis chamber to cause the reporter to fluoresce, and the emitted fluorescence is measured by a suitable detector. In the absence of the analyte of interest, no fluorescence occurs.

In some embodiments (e.g., in which a tertiary immunoassay method is implemented), the methods described herein may include steps of: (a) contacting a sample with a magnetic conjugate comprising a magnetic particle and a capture moiety configured to bind an analyte in a sample; (b) applying a magnetic field to separate the analyte from the sample; (c) contacting the magnetic conjugate with a reporter binding moiety having a tag bound thereto, the reporter binding moiety being configured to bind the analyte; (d) contacting the magnetic conjugate with a reporter having a tag binding partner bound thereto that is configured to bind the tag thereby optionally associating the reporter binding moiety bound to the tag with the reporter, wherein a concentration of the reporter binding moiety is substantially greater than a concentration of the reporter; (e) applying a magnetic field to separate the magnetic conjugate, optionally having the analyte and the reporter binding moiety associated with the reporter bound thereto; and (f) detecting the presence, absence, or level of the analyte based on detection of a signal generated by the reporter.

In the above embodiments, after the step (b) (a pulldown by a magnet to separate the analytes from the sample) is performed, and before the step (c), a magnetic field may be deactivated. Also, in some embodiments, after the step (b) and before the step (c), a volume of a sample may be removed and analyte concentration steps may be performed, as discussed above.

In some embodiments, a detection method comprises a whole cell immunoassay that targets surface analytes (e.g., biomarkers such as cell surface receptors) present on a cell of interest, thereby detecting the entire cell (e.g., a bacterium). The ability to measure whole cells can provide insights into fitness, immune disorders, cancers, and bacterial infections. In the case of strep throat, e.g. the detection of the bacterium *Streptococcus pyogenes* is highly valuable due to the prevalence of this infection in adults in children. The whole cell detection can advantageously allow detecting bacteria in complex samples, which finds use in in clinical, epidemiological, and environmental applications.

In embodiments, the whole cell immunoassay involves the use of, for detection of an analyte, a magnetic conjugate, a reporter binding moiety, and a reporter. As in other embodiments described herein, the magnetic conjugate comprises a magnetic particle and a capture moiety coupled to the magnetic particle and configured to bind an analyte. In some implementations, a magnetic conjugate comprises a magnetic particle that has a capture moiety coupled thereto that is configured to bind the analyte. The reporter binding moiety has a corresponding tag bound thereto and is configured to bind the analyte. The capture moiety of the magnetic conjugate and the reporter binding moiety, which can be antibodies specific to surface analytes on the cell of interest, can be configured to bind markers, e.g. cell receptors, on the surface of the cell analyte being detected. The capture moiety and the reporter binding moiety can be configured to bind to the same or different cell surface receptors.

The reporter has a tag binding partner bound thereto such that the tag binding partner can bind a corresponding tag thereby associating a reporter binding moiety bound to the tag with the reporter. The assay can be designed such that, for each type of a cell being detected, multiple magnetic particles and reporters are associated with the cell (via respective capture and reporter binding moieties).

In the whole cell immunoassay, when the cells of interest are present, the assay components bind the cell receptors on the surface of the cell. The resulting complex can be attracted by a magnet and can provide an optical signal that increases in intensity as the analyte concentration increases. If the cells of interest are absent from the sample, the complex does not form and the reporter system washes away during magnetic pulldown, resulting in a negative signal.

In various embodiments, methods for detecting the presence, absence, or amount of an analyte in a biological sample can include any of the above-described sandwich method, separate addition method, competitive method (comprising two types), tertiary (three binding event) method, whole cell detection, or a combination and/or variation of these methods. In some embodiments, one or more of the sandwich, separate addition, competitive, and tertiary methods can be implemented similar to respective assays described in PCT/US2018/015440 (published as WO2018140719), the disclosure of which is incorporated by reference herein in its entirety.

Non-limiting examples of analytes that can be detected include one or more of human chorionic gonadotropin (hCG), luteinizing hormone (LH)/Lutropin, prostate specific antigen (PSA), herpes simplex virus (HSV) antibodies, estrone-3-glucuronide (E3G), bacteria, hemoglobin A1C, C-reactive protein (CRP), an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof. In some embodiments, the analyte additionally or alternatively comprises one or more of N-terminal (NT)-pro hormone BNP (NT-proBNP), C-reactive protein (CRP), D-Dimer, Vitamin-D, Vitamin B12, T3, T4, Thyroid-stimulating hormone (TSH), Parathyroid hormone (PTH), Follicle stimulating hormone (FSH), Ferritin, luteinizing hormone (LH), human chorionic gonadotropin (hCG), Progesterone, Estradiol, Testosterone, Prostate-specific antigen (PSA), and Homocysteine.

In some embodiments, the analytes are or comprise whole cells, e.g., bacteria, tumor cells, or any other types of cells. Embodiments of the present disclosure can also be used to detect viruses.

It should be appreciated that embodiments of the present disclosure provide techniques for detection of any suitable analytes.

In some embodiments, the methods for detecting the presence, absence, or amount of an analyte of interest in a' biological sample can include concentrating the analyte of interest, as described above in connection with a separate addition method. In some embodiments, the methods for detecting the presence, absence, or amount of an analyte of interest in a biological sample can include some or all steps of one or both of the competitive method, and tertiary (three binding event) method.

The methods in accordance with embodiments of the present disclosure can be implemented in a suitable analysis chamber of an analytic device or system used herein. In some embodiments, the analysis chamber comprises or is a well plate including a suitable number of wells.

The analytic system can include an analysis chamber configured to receive a biological sample therein, a magnet, a light source, and a detector (e.g., a photodetector), among other components. The analytic system can include or can be associated with a magnet, which may be a permanent magnet that may be separated from the analysis chamber in order to apply a magnetic field to the analysis chamber. In some embodiments, the magnet may be an electromagnet that may be controlled to be activated or deactivated in order to apply a magnetic field to the analysis chamber. It should be appreciated that the analytic device or system in accordance with embodiments of the present disclosure can have any suitable configuration and any suitable components configured to detect the presence, absence, or amount of an analyte in a biological sample.

In some embodiments, the analytic system includes a light source connected to or otherwise associated with the analysis chamber. The light source is configured to transmit light through at least a portion of the analysis chamber.

In some embodiments, the analysis chamber may be one chamber, or two chambers, or three chambers, or four chambers. The analysis chamber may include a plurality of chambers which can be more than four chambers. In some embodiments, the plurality of chambers may be in fluid communication with one another. In some embodiments, one or more of a biological sample, a reporter, a reporter binding moiety, and a magnetic conjugate (comprising a magnetic particle and a capture moiety associated therewith) may be mixed in a first chamber of the plurality of chambers. In some embodiments, the magnetic field may be applied in a second chamber of the plurality of chambers, and a light source coupled to the analysis chamber is configured to transmit light through the second chamber. In some embodiments, the method steps described herein may each be performed in separate chambers of the analysis chamber. In some embodiments, the analysis chamber may be one chamber and all method steps may be performed in the same chamber.

In some embodiments, a photodetector may be connected to or otherwise associated with the analysis chamber (e.g., positioned as facing, in line with, opposite to the light source, or in other ways) and may be configured to detect light transmitted through the analysis chamber by the light source and thereby measure transmittance and/or absorbance of the light. In some embodiments, the photodetector may be positioned relative to the analysis chamber such that the photodetector is orthogonal to the light source (orthogonal illumination), and may be configured to detect fluorescence and/or phosphorescence of a reporter in a portion of the analysis chamber. In some embodiments, the photodetector may be positioned relative to the analysis chamber such that the photodetector is opposite to the light source (trans illumination), and may be configured to detect fluorescence and/or phosphorescence of a reporter in a portion of the analysis chamber. In some embodiments, the photodetector may be connected to the analysis chamber, in line with the light source (e.g., by way of a dichroic mirror (cis illumination)), and may be configured to detect fluorescence and/or phosphorescence of a reporter in a portion of the analysis chamber.

The photodetectors used in embodiments of the present disclosure can have various configurations. In some embodiments, a photodetector may include one or more photomultiplier tube detectors and photodiode detectors. As used herein, the term "photomultiplier" or "photomultiplier tube" refers to optical detection components that convert incident photons into electrons via the photoelectric effect and secondary electron emission. The term photomultiplier tube is meant to include devices that include separate dynodes for current multiplication as well as those devices that include one or more channel electron multipliers. As used herein, the term "optical detector" or "photodetector" refers to a device that generates an output signal when irradiated with optical energy. Thus, in its broadest sense, the term optical detector system is taken to define a device for converting energy from one form to another for the purpose of measurement of a physical quantity or for information transfer. Optical detectors include, but are not limited to, photomultipliers and photodiodes. As used herein, the term "photodiode" refers to a solid-state light detector type including, but not limited to, PN, PIN, APD, CMOS, and CCD. In some embodiments, the photodetector may include one or more of a PN based detector, a PIN based detector, an APD based detector, a CMOS based detector, and a CCD based detector.

In some embodiments, the analysis chamber comprises a photodetector as described herein. In some embodiments, the analysis chamber comprises one or more of a PN based detector, a PIN based detector, an APD based detector, a CMOS based detector, and a CCD based detector.

In various embodiments, an analytic device or system, which can be in the form of a kit, includes a sample collector configured to receive a biological sample obtained from a subject. In various embodiments, the methods in accordance with the present disclosure may involve adding a sample acquired from a subject to the analysis chamber. In some embodiments, adding the sample to the analysis chamber may include delivering the sample to the sample collector. The sample can be blood, plasma or serum, and the sample collector can be or can include a needle prick (e.g. lancet), a syringe, or another form of a sample collector configured to access blood or another bodily fluid. In some implementations, the sample collector can be a retractable element (which can be, e.g., spring-loaded) that can be safely retracted into a sample collection tube or another compartment upon collection of a biological sample (e.g. blood, plasma or serum). In some embodiments, the device for safe sample collection comprises a needle prick (e.g. lancet) or a syringe, wherein the needle prick or the syringe is attached to a cap, the cap is detachably attachable to a sample collection tube. In some embodiments, the needle prick, syringe, or another type of a sample collector is disposed in a removable cover (which can be attached to the device) configured to cover the sample collector when not in use. The removable cover and/or the sample collector can be coupled to a valve or another component configured to be activated to retract the sample collector or otherwise make the sample collector available for sample collection. In some embodiments, the cover can be configured to open automatically, and/or the sample collector can be configured to open automatically.

In some embodiments, the sample collector (e.g., a syringe) is separate from the analytic device or system. The separate sample collector can be part of a kit including the analytic system.

The needle prick, syringe, or another type of a sample collector can be in fluid communication with the interior of the analysis chamber. Thus, the sample collector may provide the sample received therein to the analysis chamber. In some embodiments, the sample collector may include an absorbent and/or wicking material, or another type of a material that facilitates delivery of the collected sample (e.g., blood, plasma or serum) to the analysis chamber.

The analytic device or system can be disposable. In some embodiments, parts of the system (e.g., a sample collector) can be disposable while other parts can be reusable. In some embodiments, some components of the system can be removable and/or disposable.

In some embodiments, one or more of the magnetic conjugate, reporter, reporter binding moiety, and reporter conjugate (comprising a reporter and a reporter binding moiety) may be disposed at the sample collector and the contacting the sample with the magnetic conjugate, reporter, reporter binding moiety, or reporter conjugate may occur at the sample collector. In some embodiments, one or more of the magnetic conjugate, reporter, reporter binding moiety, and reporter conjugate may be imbedded in a portion of the sample collector before a sample is added to the sample collector. In some embodiments, the methods described herein may include contacting the sample in the analysis chamber with a magnetic conjugate, reporter, reporter binding moiety, and/or reporter conjugate.

In some embodiments, the reporter may be a fluorescent reporter, a phosphorescent reporter, or a colorimetric reporter such as a colored particle that may be configured to measure absorbance or scattering of light (or, for example, the presence/absence of a certain color by colorimetric analysis). The reporter can have a tag binding partner such as any of the tag binding partners described hereinabove, or other binding partners, configured to bind to respective tags.

In some embodiments, the methods described herein may further include concentrating analytes of interest in the sample by applying a magnetic field to the analysis chamber after contacting the sample with the magnetic conjugate, and then reducing the volume of the sample in the analysis chamber. In some embodiments, the methods described herein may further include deactivating the magnetic field before contacting the sample with the reporter conjugate.

In some embodiments, reducing the volume of the sample in the analysis chamber may be performed by, for example, syphoning of a fraction of the volume or by removing the entire sample and resuspending the sample in a new, lesser volume.

In embodiments, the methods described herein may further include the steps of concentrating the analytes of interest in the sample by applying a magnetic field to the analysis chamber after contacting the sample with the magnetic conjugate, removing a volume of the sample from the analysis chamber, and adding a volume of buffer and/or an additional volume of the sample to the analysis chamber. In some embodiments, the methods described herein may include the step of deactivating the magnetic field before contacting the sample with the reporter conjugate.

In some embodiments, the methods described herein may include the step of adding a volume of buffer and/or additional volumes of sample to the analysis chamber.

In some embodiments, the methods described herein may include the step of removing volumes of sample from the analysis chamber after a pulldown of the magnetic conjugate (i.e., application of a magnetic field) and before or after contacting the sample with a reporter binding moiety.

In some embodiments, the reporter binding moiety comprises a reporter antibody that is labeled with biotin and the reporter is functionalized with streptavidin. In some embodiments, the reporter binding moiety, such as, e.g., the reporter antibody, is functionalized with streptavidin and the reporter is labeled with biotin.

In various embodiments, the methods described herein include or make use of various detection techniques, e.g., for detecting a reporter signal. The detection techniques may include use of a microscope, a spectrophotometer, a fluorimeter, a tube luminometer or plate luminometer, x-ray technology, magnetic fields, a scintillator, a fluorescence activated cell sorting (FACS) apparatus, a microfluidics apparatus, a bead-based apparatus, etc.

In some embodiments, a magnetic particle of a magnetic conjugate is a paramagnetic particle. In some embodiments, the paramagnetic particle is a nanoparticle, which can be, e.g., a nanobead. In some embodiments, the paramagnetic particle is a microparticle. In some embodiments, the microparticle is a microbead. The paramagnetic particle is, in various embodiments, a magnetic nano- or microbead, which allows the particle to be held and/or manipulated by magnets. In some embodiments, the paramagnetic particle is a metallic nanoparticles coated with a thin (e.g., about 2 nm in diameter) graphene-like carbon layer. In some embodiments the paramagnetic particle is coated, e.g. streptavidin- or PEG-coated. Examples magnetic particles that can be used are DYNABEADs (THERMOFISHER), MACS beads (MILTENYI BIOTEC), TURBOBEADS (TURBO-BEADS), ABSOLUTE MAG STREPTAVIDIN MAG-NETIC PARTICLES (CREATIVE DIAGNOSTICS), and GOLD NANOPARTICLES (SIGMA ALDRICH).

In some embodiments, the magnetic beads are nanoparticles with a superparamagnetic $Fe_2O_3$ core and a biocompatible outer coating. The surface of the beads can be activated, e.g., with carboxyl groups.

In some embodiments, the reporter particles described herein may include a biocompatible coating that may be activated with amine groups or carboxyl groups to facilitate amid coupling. In some embodiments, the reporter particles described herein may be activated with amine groups or carboxyl groups to facilitate amid coupling.

In some embodiments, the particles described herein may be nanoparticles (e.g. nanobeads), which are smaller than 1 micrometer in diameter (e.g. about 5 to about 500 nanometers, e.g. about 5 nanometers, or about 10 nanometers, or about 50 nanometers, or about 100 nanometers, or about 250 nanometers, or about 500 nanometers). In some embodiments, the nanoparticles (e.g. nanobeads) have a mean particle diameter of 25-500 nm+/−5 nm, 25-500 nm+/−nm, 25-500 nm+/−15 nm, 25-500 nm+/−20 nm, 25-500 nm+/−25 nm, 25-500 nm+/−30 nm, 25-500 nm+/−35 nm, 25- 500 nm+/−40 nm, 25-500 nm+/−45 nm, or 25-500 nm+/−50 nm. In some embodiments, the nanoparticles (e.g. nanobeads) have a mean particle diameter of about 20 to about 200 nm.

In some embodiments, the nanoparticles (e.g. nanobeads) are smaller than 1 micrometer in diameter (e.g. about 5 to about 500 nanometers, e.g. about 5 nanometers, or about 10 nanometers, or about 50 nanometers, or about 100 nanometers, or about 250 nanometers, or about 500 nanometers). In some embodiments, the nanoparticles (e.g. nanobeads) have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm. In some embodiments, the nanoparticles (e.g. nanobeads) have a mean particle diameter of about 20 to about 200 nm. In some embodiments, the magnetic particle may be a magnetic nanoparticle (e.g. nanobead) that is composed of oxides, such as ferrites, maghemite, magnetite, or iron oxide, optionally modified by surfactants, silica, silicones or phosphoric acid derivatives. In some embodiments, the nanoparticle (e.g. nanobead) is composed of ferrites with a shell (e.g. a silica shell, optionally modified). In some embodiments, the magnetic nanoparticle is metallic (e.g. iron, cobalt, etc.). In some embodiments, the magnetic nanoparticle is a metallic nanoparticle comprising a shell (e.g. of gentle oxidation, surfactants, polymers and metals (e.g. of gold, graphene, palladium, platinum, etc.)).

In some embodiments, a particle described herein may be a nanoparticle that comprises one or more quantum dots In some embodiments, the nanoparticle comprises a metal core and one or more quantum dots. In some embodiments, the nanoparticle comprises a metal core that may be studded with one or more quantum dots. In some embodiments, the nanoparticle comprises a metal core that may be studded with a plurality of quantum dots. Quantum dots are discrete nanoparticles that have properties similar to bulk semiconductors such that when exposed to electromagnetic energy they in turn emit energy. Quantum dots can be engineered to be sensitive to energy in the infrared region, the visible spectrum, and even ultraviolet range through changes in size and composition. Further, they can be designed to be either photoluminescent or photovoltaic, producing either light or energy, respectively.

In some embodiments, the reporter may be a nanoparticle (e.g. nanobead), which may comprise one or more quantum dots. In some embodiments, the reporter comprises a metal core and one or more quantum dots. In some embodiments, the reporter comprises a metal core that may be studded with one or more quantum dots. In some embodiments, the reporter comprises a metal core that may be studded with a plurality of quantum dots.

In some embodiments, the reporter may comprise one or more quantum dots or quantum-dot-studded particles. In some embodiments, the reporter may comprise one or more quantum dots or quantum-dot-studded particles. In some embodiments, the reporter may comprise a plurality of quantum dots or quantum-dot-studded particles.

Examples of quantum dots, e.g. produced by colloidal methods, include, but are not limited to, cadmium-selenide (CdSe), cadmium-sulfide (CdS), indium-arsenide (InAs), and indium-phosphide (InP) cadmium-tellurium-sulfide (CdTeS). The number of atoms that comprise a quantum dot can range from 100 to 100,000, typically with a diameter ranging from 2 to 20 nm (e.g., 2, 3, 4, 5, 6, 7, 8, 9, 10, 11, 12, 13, 14, 15, 16, 17, 18, 19, 20, 2.5, 3.5, 4.5, 5.5, 6.5, 7.5, 8.5, 9.5, 10.5, 11.5, 12.5, 13.5, 14.5, 15.5, 16.5, 17.5, 18.5, 19.5, 20.5 nm).

In some embodiments, particle materials, including quantum dot materials, include, but are not limited to, carbon, colloidal gold, germanium, indium arsenide, indium antimonide, gallium arsenide, gallium nitride, cadmium/selenium/telluride, lead, lead oxide, lead sulfide, lead selenide, indium gallium phosphide, silicon, colloidal silver, mercury cadmium telluride, iron, iron oxide, cobalt, graphene, lanthanum, cerium, strontium carbonate, manganese, manganese oxide, nickel oxide, platinum, lithium, lithium titanate, tantalum, copper, palladium, molybdenum, boron carbide, silicon carbide, titanium carbide, tungsten oxide, aluminum, niobium, thulium, aluminum nitride, tin, aluminum oxide, tin oxide, antimony, dysprosium, paseodynium, antimony oxide, erbium, rhenium, barium, ruthenium, beryllium, samarium, bismuth oxide, boron, gadolinium, boron nitride, vanadium oxide, strontium, ytterbium, zirconium, diamond (C), Silicon (Si), germanium (Ge), silicon carbide (SIC), silicon-germanium (SiGe), aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), aluminium gallium arsenide (AlGaAs), indium gallium arsenide (InGaAs, InxGai_xAs), indium gallium phosphide (InGaP), aluminum indium arsenide (AlInAs), aluminum indium antimonide (AlInSb), gallium arsenide nitride (GaAsN), gallium arsenide phosphide (GaAsP), aluminum gallium nitride (AlGaN), aluminum gallium phosphide (AlGaP), indium gallium nitride (InGaN), indium arsenide antimonide (InAsSb), indium gallium antimonide (InGaSb), aluminum gallium indium phosphide (AlGaInP, also InAlGaP, InGaAlP, AlInGaP), aluminum gallium arsenide phosphide (AlGaAsP), indium gallium arsenide phosphide (InGaAsP), aluminum indium arsenide phosphide (AlInAsP), aluminum gallium arsenide nitride (AlGaAsN), indium gallium arsenide nitride (InGaAsN), indium aluminium arsenide nitride (InAlAsN), gallium arsenide antimonide nitride (GaAsSbN), gallium indium nitride arsenide antimonide (GaInNAsSb), gallium indium arsenide antimonide phosphide (GaInAsSbP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cadmium zinc telluride (CdZnTe, "CZT"), mercury cadmium telluride (HgCdTe), mercury zinc telluride (HgZnTe), mercury zinc selenide (HgZnSe), cuprous chloride (CuCl), lead selenide (PbSe), lead sulfide (PbS), lead telluride (PbTe), tin sulfide (SnS), tin telluride (SnTe), lead tin telluride (PbSnTe), thallium tin telluride ($Ti_2SnTe_5$), thallium germanium telluride ($Tl_2GeTe_5$), bismuth telluride ($Bi_2Te_3$), cadmium phosphide ($Cd_3P_2$), cadmium arsenide ($Cd_3As_2$), cadmium antimonide ($Cd_3Sb_2$), zinc phosphide ($Zn_3P_2$), zinc arsenide ($Zn_3As_2$), zinc antimonide ($Zn_3Sb_2$), lead(II) iodide ($Pbl_2$), molybdenum disulfide ($MoS_2$), gallium selenide (GaSe), tin sulfide (SnS), bismuth sulfide ($Bi_2S_3$), copper indium gallium selenide (CIGS), platinum silicide (PtSi), bismuth(III) iodide ($BiI_3$), mercury(II) iodide ($HgI_2$), thallium(I) bromide (TlBr), titanium dioxide: anatase ($TiO_2$), copper(I) oxide ($Cu_2O$), copper(II) oxide (CuO), uranium dioxide ($UO_2$), uranium trioxide ($UO_3$), and the like.

In various embodiments, the magnetic field is applied using an external magnet. In various embodiments, the magnet is a permanent magnet (e.g. neodymium iron boron (NdFeB), samarium cobalt (SmCo), alnico, and ceramic or ferrite magnets). In various embodiments, the magnet is a temporary magnet. In various embodiments, the magnet is an electromagnet.

In various embodiments, the detection of the reporter is undertaken near the magnetic field. In various embodiments, the detection of the reporter is undertaken away from the magnetic field as in, for example, performed in a chamber that is separate from a chamber in which a magnetic pull down step is performed.

In some embodiments, the method provides nanomolar, or picomolar, or femtomolar scale sensitivity.

In various aspects, the present invention provides a kit suitable for the method of any one of the embodiments disclosed herein. The kit can be for an immunoassay in which a concentration of a reporter binding moiety is substantially greater than a concentration of a reporter. The kit may comprise a magnetic conjugate, a reporter binding moiety, and a reporter, and a concentration of the reporter binding moiety is substantially greater than a concentration of the reporter.

Optionally, the above-described components of the kits of the present technology are packed in suitable containers and labeled for diagnosis of a corresponding disease or condition, or are labeled for corresponding other purpose. The above-mentioned components may be stored in unit or multi-use containers, for example, sealed ampoules, vials, bottles, syringes, and test tubes, as an aqueous, preferably sterile, solution or as a lyophilized, preferably sterile, formulation for reconstitution. For example, the assay reagents of the present technology can be lyophilized to obviate requirement for cold chain shipping and storage. For example, in some embodiments, all reagents except the Magnesium Acetate Mg $(CH_3COO)_2$ are lyophilized in the bottom of the assay tube and the Mg $(CH_3COO)_2$ is lyophilized on the lid: this prevents the 5' to 3' DNA polymerase from occurring until the Mg $(CH_3COO)_2$ is mixed with the other assay reagents.

The kit may further comprise a second container which holds a buffer or other ingredients suitable for diluting the sample towards a higher volume. Furthermore, the kit may comprise instructions for carrying out the assay. The containers may be formed from a variety of materials such as glass or plastic and may have a sterile access. The kit may further comprise more containers comprising an acceptable buffer. The kit may further comprise a device for collecting a biological sample. It may further include other materials desirable from a commercial and user standpoint, including other buffers, diluents, filters, needles, and syringes. The kits may optionally include instructions customarily included in commercial packages of diagnostic products, which include information about, for example, the indications, usage, manufacture, and/or warnings concerning the use of such diagnostic products. The kits may further include a color or fluorescent scale for comparison for diagnosis. The kit components (e.g., reagents) can be packaged in a suitable container. The kit can further comprise instructions for using the kit.

In some embodiments, the kit further comprises a device that collects the biological sample (e.g., blood, serum, plasma, urine, or another type of sample) in a safe manner. In some embodiments (e.g., for analysis of blood content), the device comprises a needle and a safety syringe (e.g. a Luer-type syringe). In some embodiments, the device comprises spring-loaded retractable needle and a syringe. It should be appreciated that the device can be any type of a device for collecting a sample that can be any of whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, Rheum, lymph, and pus. Also, in some embodiments, the kit does not include a sample collection device.

In some embodiments, the kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit.

In various aspects, a sample can be obtained from a subject that is a human subject. Additionally, in some embodiments, a subject is a mammal different from a human.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

As used herein, the term "sample" may refer to a solution, suspension, mixture, or undiluted amount of bodily or another fluid that may or may not include an analyte of interest. A sample, as used herein, may include water and/or a buffer.

As used herein, the term "bodily fluid" may refer to any fluid that can be isolated from the body of an individual and includes, but is not limited to whole blood, plasma, serum, bile, saliva, urine, tears, perspiration, cerebrospinal fluid (CSF), semen, swabbed samples (e.g. cheek swabs, throat swabs, etc.), mucus, sputum, menstrual blood, menstrual fluid, vaginal mucus, amniotic fluid, synovial fluid, breast milk, ear wax, preejaculate, lochia, Rheum, lymph, pus, and the like. In some embodiments, bodily fluid may more particularly refer to whole blood, serum, urine, saliva, swabbed samples, mucus, or semen. In certain embodiments, bodily fluid may more particularly refer to whole blood, serum, urine, or saliva. In some embodiments, the bodily fluid may include an analyte of interest (e.g., a biomarker).

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EXAMPLES

The examples herein are provided to illustrate advantages and benefits of the present technology and to further assist a person of ordinary skill in the art with practicing the method for treating a cancer of the present technology. The examples herein are also presented in order to more fully illustrate the certain aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Example 1. Dependence of Immunoassay
Performance on Concentration of Reporter Binding
Moiety FIG. 3 illustrates results of a titration of a reporter binding moiety (an antibody, in this example) with a tag in an assay in accordance with embodiments of the present disclosure. A detected signal (Y-axis, in fluorescence units, MM) versus a concentration of an analyte of interest (hCG, in mIU/ml) (X-axis), is shown for different concentrations of a reporter binding moiety (40 pM, 80 pM, 160 pM, 1 nM, 5 nM, 25 nM, 125 nM, 625 nM, and 3.125 uM). As shown in FIG. 3, the concentration of a reporter binding moiety of about 5 nM achieves the higher signal of the entire range of concentrations of the reporter. As also shown, there is a noticeable jump in the signal values between the curves representing 160 pM and 1 nM concentrations of the reporter binding moiety, respectively, and the smaller jump between the curves representing 1 nM and 5 nM concentrations of the reporter binding moiety, respectively. FIG. 3 demonstrates that a concentration of a reporter binding moiety in a nanomolar range dramatically boosts performance (i.e. intensity of fluorescence is increased).

Example 2. Dependence of Immunoassay
Performance on Concentration of Reporter

FIG. 4 is illustrates results of a titration of the reporter in the assay, showing a signal resulting from non-specific and/or off-target binding (in fluorescence units, MM) as it varies depending on a concentration of a reporter (quantum dots). Three replicates and an average of the replicates are shown. In this example, the concentration of the reporter that provides the lowest background (i.e. best performance) is 20 pM. FIG. 4 demonstrates that the non-specific signal (background noise) is greater (and thus worse) when the reporter is in a nanomolar range (~5 MM fluorescence units) than when the reporter is in a picomolar range (0.01-0.18 MM fluorescence units). The data shown in FIG. 4 was obtained using a Luteinizing hormone (LH) system on a negative control sample which should have little to no LH.

Example 3: Improved Limits of Detection

In this example, a pair of antibodies against LH were analyzed using the concentration difference ("kinetic engineering" methods described herein. The antibody pair has KDs of 2.3 pM and 6.3 pM (KAs of $4.4 \times 10^{11}$ and $1.6 \times 10^{11}$) respectively.

Relevant parameters include:

| Kinetic Parameters | |
| --- | --- |
| Association rate constant | $5.8 \times 10^6$ 1/Ms |
| Dissociation rate constant | $1.3 \times 10^{-5}$ 1/s |
| Affinity constant | $K_A = 4.4 \times 10^{11}$ 1/M; |
| | $K_D = 2.3 \times 10^{-12}$M (=2.3 pM) |
| Determination Method | SPR analysis (ProteOn XPR36) |
| Determination antigen | LH, Scripps Laboratories |
| | (Cat L0815, Lot 2360102) |
| Kinetic Parameters | |
| Association rate constant | $5.4 \times 10^6$ 1/Ms |
| Dissociation rate constant | $3.4 \times 10^{-5}$ 1/s |
| Affinity constant | $K_A = 1.6 \times 10^{11}$ 1/M; |
| | $K_D = 6.3 \times 10^{-12}$M (=6.3 pM) |
| Determination method | SPR analysis (ProteOn XPR36) |
| Determination antigen | LH, Scripps Laboratories |
| | (Cat L0815, Lot 2360102) |

With these antibodies in a traditional equilibrium, non-kinetically engineered, immunoassay one would expect that one should not be able to achieve an LOD lower than 6.3 pM.

Here, a LOD of 7.7 fM was achieved with these antibodies using the present kinetic engineering methods. This is nearly 1000× lower than the theoretical limit in a traditional immunoassay and ~5000× lower than the practical limit in a traditional immunoassay. See FIG. 5.

Further, in this example, a pair of antibodies against PSA were analyzed using the concentration difference ("kinetic engineering" methods described herein. The antibody pair has KDs of 7.5 pM and 11 pM (KAs of $1.3\times10^{11}$ and $1\times10^{11}$) respectively.

Relevant parameters include:

| Kinetic Parameters | |
| --- | --- |
| Association rate constant | $2.0 \times 10^6$ 1/Ms |
| Dissociation rate constant | $1.5 \times 10^{-5}$ 1/s |
| Affinity constant | $K_A = 1.3 \times 10^{11}$ 1/M; $K_D = 2.3 \times 10^{-12}$M (=2.3 pM) |
| Determination Method | SPR analysis (ProteOn XPR36) |
| Determination antigen | PSA human, Scripps (Cat P0725, Lot 2470302) |

| Kinetic Parameters | |
| --- | --- |
| Association rate constant | Not Determined (N/D) |
| Dissociation rate constant | N/D |
| Affinity constant | $1 \times 10^{11}$ 1/M |
| Determination method | Radioimmunoassay (RIA) |
| Determination antigen | PSA, Aalto (Cat AJ 3032, Lot 1133) |

With these antibodies in a traditional equilibrium, non-kinetically engineered, immunoassay one would expect that one should not be able to achieve an LOD lower than 11 pM.

Here, a LOD of 15.7 fM was achieved with these antibodies using the present kinetic engineering methods. This is nearly 1000× lower than the theoretical limit in a traditional immunoassay and ~5000× lower than the practical limit in a traditional immunoassay. See FIG. 6.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

EQUIVALENTS

While the invention has been disclosed in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for detecting the presence, absence, or amount of an analyte in a biological sample, the method comprising:

(a) contacting the biological sample with a magnetic conjugate comprising a magnetic particle and a capture moiety comprising a first antibody configured to bind the analyte in the biological sample;

(b) contacting the magnetic conjugate and the bound analyte with a reporter binding moiety comprising a second antibody and a biotin tag bound thereto, wherein the capture moiety and the reporter binding moiety bind different portions of the analyte, and wherein the reporter binding moiety is present at a concentration of about 1 nM to about 600 nM;

(c) contacting a complex comprising the magnetic conjugate, the analyte, and the reporter binding moiety with a reporter comprising a streptavidin tag binding partner that is configured to bind the biotin tag of the reporter binding moiety, wherein the reporter comprises a particle studded with a plurality of quantum-dots, and wherein the reporter is present at a concentration of about 10 pM to about 140 pM;

(d) applying a magnetic field to separate a detectable complex comprising the magnetic conjugate, the analyte, the reporter binding moiety and the reporter bound thereto; and (e) detecting the presence, absence, or amount of the analyte based on detection of a signal generated by the reporter.

2. The method of claim 1, wherein the reporter binding moiety is present at a concentration of about 1 nM to about 10 nM.

3. The method of claim 2, wherein the reporter binding moiety is present at a concentration of about 5 nM.

4. The method of claim 1, wherein the reporter is present at a concentration of about 15 pM to about 25 pM.

5. The method of claim 4, wherein the reporter is present at a concentration of about 20 pM.

6. The method of claim 1, wherein the reporter comprises a metal core and a silica shell, wherein the silica shell is impregnated with one or more quantum dots.

7. The method of claim 1, wherein the analyte is selected human chorionic gonadotropin (hCG), luteinizing hormone (LH)/Lutropin, prostate specific antigen (PSA), herpes simplex virus (HSV) antibodies, estrone-3-glucuronide (E3G), bacteria, hemoglobin A1C, C-reactive protein (CRP), an inflammation biomarker, troponin, lyme disease antigen, lyme disease antibodies, an LDL biomarker, an HDL biomarker, a total cholesterol biomarker, thyroid stimulating hormone, a hepatitis C virus biomarker, a rhino virus biomarker, an influenza virus biomarker, a liver function biomarker, estrogen, progesterone, lactic acid, and combinations thereof.

8. The method of claim 1, wherein the biological sample is selected from whole blood, plasma, serum, bile, saliva, urine, tears, perspiration, cerebrospinal fluid (CSF), semen, mucus, sputum, menstrual blood, menstrual fluid, vaginal mucus, amniotic fluid, synovial fluid, breast milk, ear wax, preejaculate, lochia, rheum, lymph, and pus.

9. The method of claim 1, wherein the analyte comprises an antibody and the capture moiety comprises an antigen configured to bind the antibody.

10. The method of claim 9, wherein the reporter binding moiety comprises a secondary antibody configured to bind the antigen.

11. The method of claim 1, wherein the method detects an amount of antibodies present in the biological sample.

12. The method of claim 1, further comprising pre-treating the biological sample with a magnetic conjugate comprising a magnetic particle and a moiety configured to bind contaminant antibodies and/or non-antibody moieties.

*     *     *     *     *